United States Patent
Han

(10) Patent No.: US 11,260,041 B2
(45) Date of Patent: Mar. 1, 2022

(54) PHORBOL ESTER COMPOSITIONS AND METHODS OF USE FOR TREATING OR REDUCING THE DURATION OF CYTOPENIA

(71) Applicant: BIOSUCCESS BIOTECH CO., LTD., San Jose, CA (US)

(72) Inventor: Zheng Tao Han, Eugene, OR (US)

(73) Assignee: Biosuccess Biotech Co. Ltd., San Jose, CA (US)

( * ) Notice: Subject to any disclaimer, the term of this patent is extended or adjusted under 35 U.S.C. 154(b) by 0 days.

(21) Appl. No.: 14/930,849

(22) Filed: Nov. 3, 2015

(65) Prior Publication Data

US 2016/0120836 A1    May 5, 2016

Related U.S. Application Data

(60) Provisional application No. 62/074,133, filed on Nov. 3, 2014.

(51) Int. Cl.
| | | |
|---|---|---|
| *A61K 31/23* | (2006.01) | |
| *A61K 38/19* | (2006.01) | |
| *A61K 38/18* | (2006.01) | |
| *A61K 31/235* | (2006.01) | |
| *A61K 31/22* | (2006.01) | |

(52) U.S. Cl.
CPC ............ *A61K 31/23* (2013.01); *A61K 31/22* (2013.01); *A61K 31/235* (2013.01); *A61K 38/1816* (2013.01); *A61K 38/193* (2013.01)

(58) Field of Classification Search
CPC .. A61K 2300/00; A61K 31/22; A61K 31/235; A61K 31/23; A61K 38/1816; A61K 38/193; A61P 35/02; A61P 43/00; A61P 7/00; A61P 7/04; A61P 7/06
USPC ......................................................... 514/68
See application file for complete search history.

(56) References Cited

U.S. PATENT DOCUMENTS

| | | | | |
|---|---|---|---|---|
| 6,063,814 A | * | 5/2000 | Chang ................ | A61K 31/216 514/510 |
| 6,080,784 A | * | 6/2000 | Driedger ............. | C07C 69/00 514/480 |
| 7,345,031 B2 | * | 3/2008 | Christian ............ | A61K 31/704 514/62 |
| 9,132,113 B2 | * | 9/2015 | Han ..................... | A61K 31/55 |
| 9,597,394 B2 | * | 3/2017 | Segal .................. | A61K 39/145 |
| 2008/0226589 A1 | * | 9/2008 | Han ..................... | A61K 31/55 424/85.2 |
| 2014/0017196 A1 | * | 1/2014 | Han ..................... | A61K 31/381 424/85.2 |
| 2014/0206762 A1 | | 7/2014 | Han et al. | |
| 2017/0096386 A1 | * | 4/2017 | Chang ................. | A61P 39/02 |

FOREIGN PATENT DOCUMENTS

| | | |
|---|---|---|
| AU | 2013-209524 A1 | 8/2014 |
| AU | 2013209524 A1 | 8/2014 |
| CN | 102380090 A | 3/2012 |
| WO | 2013/110006 A2 | 7/2013 |

OTHER PUBLICATIONS

Spiekerman et al. (DN 1999:265218; DN 122:29298, abstract of British Journal of Haematology (1994), 88(3) 506-14).*
Kothari SS et al. (Blood Cells Mol. Dis: 21 (3): 192-200).*
Advani et al. (Indian J Med Pediatr Oncol. Jul.-Sep. 2010; 31(3): 79-82).*
Voloshin et al. (Blood. Sep. 22, 2011; 118(12): 3426-3435. Prepublished online Jun. 17, 2011. doi: 10.1182/blood-2010-11-320812, 892 dated Jun. 22, 2020).*
Ryves et al., "Activation of the PKC-isotypes $\alpha,\beta_1$, $\gamma$, $\delta$ and $\epsilon$ by phorbol esters of different biological activities", FEBS, 288(1, 2):5-9 (1991).
Han et al., "Effect of intravenous infusions of 12-O-tetradecanoylphorbol-13-acetate (TPA) in patients with myelocytic leukemia: Preliminary studies on therapeutic efficacy and toxicity," PNAS, 95(9):5357-5361 (1998).
Stefanovic et al., "Lymphocyte PC-1 activity in patients on maintenance hemodialysis treated with erythropoietin and 1-$\alpha$-D3," Annals Clin. Biochem., 42(1): 55-60 (2005) (Abstract).
Spivak et al., "Tumor-promoting phorbol esters support the in vitro proliferation of murine pluripotent hematopoietic stem cells," J. Clin. Invest., 83(1): 100-107 (1989).
Office Action dated May 11, 2020 by the State Intellectual Property Office of People's Republic of China in Chinese Application No. 201580071387.2.

* cited by examiner

*Primary Examiner* — Sabiha N Qazi
(74) *Attorney, Agent, or Firm* — Sughrue Mion, PLLC

(57) ABSTRACT

Methods and compositions containing a phorbol ester or a derivative of a phorbol ester in combination with G-CSF or in combination with EPO, are provided for the treatment of cytopenia in mammalian subjects. The compositions and methods also reduce the duration of cytopenia such as neutropenia, thrombocytopenia, and/or anemia.

11 Claims, 2 Drawing Sheets

PHORBOL ESTER COMPOSITIONS AND METHODS OF USE FOR TREATING OR REDUCING THE DURATION OF CYTOPENIA

TECHNICAL FIELD

The present invention relates to the use of phorbol esters for the treatment of cytopenia. Specifically, the present invention relates to the use of phorbol esters, such as 12-O-tetradecanoylphorbol-13-acetate (TPA) or phorbol-12-myristate (PMA), and G-CSF in the treatment and reduction of neutropenia and thrombocytopenia in patients with a neoplastic disease. The present invention also relates to the use of phorbol esters, such as TPA and erythropoeitin (EPO) for the treatment of anemia in patients.

BACKGROUND

Plants have historically served many medicinal purposes. The World Health Organization (WHO) estimates that 4 billion people, 80% of the world population, presently use herbal medicine for some aspect of primary health care. (WHO Fact sheet Fact sheet No 134 December 2008) However, it can be difficult to isolate the specific compound that has the medicinal effect and to reproduce it on a commercial scale. Additionally, while active compounds may be isolated from a plant, the other parts of a plant such as the minerals, vitamins, volatile oils, glycosides, alkaloids, bioflavanoids, and other substances may also be involved in the functioning of the active ingredient or the medicinal effect for which the plant is known, making the use, purification and commercialization of plant based pharmaceutical agents a challenge.

Phorbol is a natural, plant-derived organic compound of the tigliane family of diterpenes. It was first isolated in 1934 as a hydrolysis product of croton oil derived from the seeds of *Croton tiglium*, a leafy shrub of the Euphorbiaceae family that is native to Southeastern Asia. Various esters of phorbol have important biological properties including the reported ability to mimic diacylglycerols and activate protein kinase C (PKC); and to modulate downstream cell signaling pathways including the mitogen-activated protein kinase (MAPK) pathways. Phorbol esters are additionally thought to bind to chimaerins, the Ras activator RasGRP, and the vesicle-priming protein Munc-13 (Brose N, Rosenmund C., J Cell Sci; 115:4399-411 (2002)). Some phorbol esters also induce nuclear factor-kappa B (NF-κB). The most notable physiological property of phorbol esters is their reported capacity to act as tumor promoters. (Blumberg, 1988; Goel, G et al., Int, Journal of Toxicology 26, 279-288 (2007)).

12-O-tetradecanoylphorbol-13-acetate (TPA), also called phorbol-12-myristate-13-acetate (PMA), is a phorbol ester used in models of carcinogenesis as an inducer for differentiation and/or apoptosis in multiple cell lines and primary cells. TPA has also been reported to cause an increase in circulating white blood cells and neutrophils in patients whose bone marrow function has been depressed by chemotherapy (Han Z. T. et al. Proc. Natl. Acad. Sci. 95, 5363-5365 (1998)). However, due to a variety of factors, including caustic reactions when contacted with the skin and concerns for its potential toxicity, TPA has not been shown to be an effective adjuvant to chemotherapy. Indeed, as phorbol esters play a key role in activation of protein kinase C, which triggers various cellular responses resulting in inflammatory responses and tumor development (Goel et al., Int, Journal of Toxicology 26, 279-288 (2007)), phorbol esters would generally be excluded from possible treatment candidates for neoplasms including cancer.

Cancer is one of the leading causes of death worldwide accounting for 7.6 million deaths (around 13% of all deaths) in 2008 (GLOBOCAN 2008 (IARC) (*Section of Cancer Information* (Aug. 12, 2011)). Globally, 12,662,600 new cases were diagnosed in 2008. (2008 (GLOBOCAN 2008 (IARC). In the U.S. alone, 1,596,670 new cases of cancer were diagnosed in 2011 (Cancer Facts & Figures—2011, American Cancer Society (ACS), Atlanta, Ga., 2011).

Cancer treatments generally involve a combination of surgery, chemotherapy, hormonal therapy and/or radiation treatment to eradicate neoplastic cells in a patient. However, current therapeutics for neoplasms have a number of drawbacks including insufficient potency and intolerable side effects. Surgery, for example, may be contraindicated due to the health of a patient. Additionally, it may be difficult to obtain clear margins around a tumor, resulting in some neoplastic tissue being left behind and an increased chance of recurrence of the disease.

Generally, chemotherapeutics act by killing cells that divide rapidly, one of the main properties of most cancer cells. However, they also harm normal cells that divide rapidly such as cells in bone marrow, the digestive tract and hair follicles. They frequently have significant side effects including severe nausea, bone marrow depression, and immunosuppression.

Ionizing radiation works by damaging the DNA of exposed tissue. However, while targeted, it can still damage normal cells as well as neoplasms and can have side effects such as anemia, nausea and vomiting, poor appetite, weight loss, constipation, diarrhea, hair loss, and infertility.

For many patients, the toxic side effects of current therapies diminish their quality of life to such an extent they simply stop taking their medications. For others, therapeutic schedules are so complicated and inconvenient that compliance is limited. Other patients experience excellent results initially, but suffer relapses despite full compliance with therapeutic regimens. There is clearly a need for new and more effective treatments for neoplasms and to manage the side effects of current treatments for neoplasms including cancer.

SUMMARY OF THE INVENTION

The present invention relates to compositions containing and methods of using phorbol esters of Formula I in combination with G-CSF. The compositions and methods described herein are effective in treating and reducing the duration of neutropenia and thrombocytopenia in patients with neoplastic conditions.

In an embodiment, the present invention relates to a method of treating cytopenia comprising administering to a mammalian subject in need thereof, a phorbol ester of Formula I (as described herein), pharmaceutically-acceptable salt, isomer, enantiomer, solvate, hydrate, polymorph or prodrug thereof, wherein $R_1$ and $R_2$ are selected from the group consisting of hydrogen, hydroxyl,

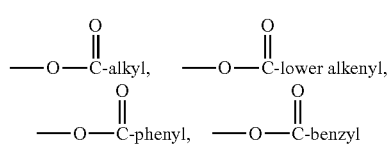

and substituted derivatives thereof, $R_3$ is selected from hydrogen,

and substituted derivatives thereof;
in combination with a granulocyte-colony stimulating factor (G-CSF).

In a particular embodiment, the present invention relates to a a method of treating neutropenia and/or thrombocytopenia comprising administering to a mammalian subject in need thereof, a combination of a phorbol ester of Formula I, pharmaceutically-acceptable salt, isomer, enantiomer, solvate, hydrate, polymorph or prodrug thereof; in combination with a granulocyte-colony stimulating factor (G-CSF).

In another embodiment, the present invention relates to a method of treating cytopenia comprising administering to a mammalian subject in need thereof, a phorbol ester of Formula I, pharmaceutically-acceptable salt, isomer, enantiomer, solvate, hydrate, polymorph or prodrug thereof; in combination with an erythropoietin (EPO).

In a particular embodiment, the present invention relates to a a method of treating anemia comprising administering to a mammalian subject in need thereof, a phorbol ester of Formula I, pharmaceutically-acceptable salt, isomer, enantiomer, solvate, hydrate, polymorph or prodrug thereof; in combination with an erythropoietin (EPO).

In methods of the present invention, $R_1$ or $R_2$ of Formula I is

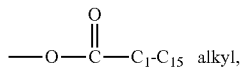

the remaining $R_1$ or $R_2$ is

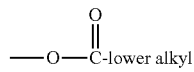

and $R_3$ of Formula I is hydrogen.

In particular, in the methods of the invention, the phorbol ester is phorbol 13-butyrate, phorbol 12-decanoate, phorbol 13-decanoate, phorbol 12,13-diacetate, phorbol 13,20-diacetate, phorbol 12,13-dibenzoate, phorbol 12,13-dibutyrate, phorbol 12,13-didecanoate, phorbol 12,13-dihexanoate, phorbol 12,13-dipropionate, phorbol 12-myristate, phorbol 13-myristate, phorbol 12,13,20-triacetate, 12-deoxyphorbol 13-angelate, 12-deoxyphorbol 13-angelate 20-acetate, 12-deoxyphorbol 13-isobutyrate, 12-deoxyphorbol 13-isobutyrate-20-acetate, 12-deoxyphorbol 13-phenylacetate, 12-deoxyphorbol 13-phenylacetate 20-acetate, 12-deoxyphorbol 13-tetradecanoate, phorbol 12-tigliate 13-decanoate, 12-deoxyphorbol 13-acetate, phorbol 12-acetate, or phorbol 13-acetate.

In a preferred embodiment, the phorbol ester is 12-O-tetradecanoylphorbol-13-acetate (TPA).

The methods of the present invention, may further comprise administering at least one secondary or adjunctive therapeutic agent.

In certain embodiments of the present invention, G-CSF is administered to said subject in a coordinate administration protocol, simultaneously with, prior to, or after, administration of said phorbol ester of Formula I.

In certain embodiments of the present invention, EPO is administered to said subject in a coordinate administration protocol, simultaneously with, prior to, or after, administration of said phorbol ester of Formula I.

The methods of the present invention involve administering the phorbol ester of Formula I in an effective amount comprising between about 10 and 1500 µg of said phorbol ester of Formula I every day or every other day.

In certain embodiments, the methods of the present invention involve administering the phorbol ester of Formula I in an effective amount comprising between about 150 to 500 µg of said phorbol ester or derivative compound of Formula I every day or every other day.

In preferred embodiment of the present invention, the combination of the phorbol ester of Formula I and G-CSF increases absolute neutrophil count (ANC) of the mammalian subject to above 1500/mm³.

In another preferred embodiment, the combination of the phorbol ester of Formula I and G-CSF increases platelet levels of the mammalian subject to above 100,000/µl.

In a certain preferred embodiment of the present invention, the combination of the phorbol ester of Formula I and EPO increases a complete blood count (CBC) level measured in a complete blood count by at least 10%.

In another preferred embodiment, wherein the combination of the phorbol ester of Formula I and EPO increases a hemoglobin level of the mammalian subject to above a normal hemoglobin level.

In a preferred embodiment, the methods of the present invention involve treating or reducing cytopenia such as neutropenia, thrombocytopenia and/or anemia, in a human with acute myeloid leukemia (AML).

In another embodiment, the present invention relates to compositions containing a phorbol ester of Formula I and G-CSF.

In a preferred embodiment, the phorbol ester of Formula I is present in an effective amount sufficient to treat or reduce the duration of cytopenia, such as neutropenia and/or thrombocytopenia.

In a preferred embodiment, the compositions of the present invention contain TPA as the phorbol ester, and the TPA and G-CSF are present in an effective amount to treat or reduce the duration of cytopenia, such as neutropenia and/or thrombocytopenia. In a particularly preferred embodiment, the effective amount may be a synergistically effective amount to treat or reduce the duration of neutropenia and/or thrombocytopenia.

The present invention also relates to compositions containing a phorbol ester of Formula I and EPO.

In a preferred embodiment, the phorbol ester of Formula I is present in an effective amount sufficient to treat or reduce the duration of cytopenia, such as anemia.

In a preferred embodiment, the compositions of the present invention contain TPA as the phorbol ester, and the TPA and EPO are present in an effective amount to treat or reduce the duration of cytopenia, such as anemia. In a particularly preferred embodiment, the effective amount may be a synergistically effective amount to treat or reduce the duration of anemia.

In another embodiment, the neutropenia, thrombocytopenia and/or anemia is related to treatment of neoplasms. Such neoplasms may be malignant or benign. In some embodiments, neoplasms may be solid or non-solid cancers. In other embodiments, the neoplasms may be relapses. In another embodiment, the neoplasms may be refractory.

Exemplary neoplasms include, but are not limited to, hematologic malignancies/bone marrow disorders, including, but not limited to, leukemia, including acute myeloid leukemia (AML), chronic myeloid leukemia (CML), chronic myeloid leukemia blast crisis, myelodysplasia, and myeloproliferative syndrome; lymphoma, including Hodgkin's and non-Hodgkin's lymphoma; subcutaneous adenocarcinoma; ovarian teratocarcinoma; liver cancer; breast cancer; bone cancer; lung cancer; pancreatic cancer; non-small cell lung cancer; and prostate cancer. Other neoplastic conditions amenable to treatment using the methods and compositions as described herein include other cancer disorders and conditions, including solid tumors of various types.

In yet another embodiment, the phorbol esters and derivatives of phorbol esters as described herein may be used to modulate cell signaling pathways. Such modulation may have a variety of results, for example, in some embodiments, the use of compositions containing phorbol esters and derivatives of phorbol esters may increase white blood cell counts in mammalian subjects. In another embodiment, compositions containing phorbol esters and/or phorbol ester derivatives may alter the release of Th1 cytokines in mammalian subjects. In a further embodiment, compositions containing phorbol esters and/or phorbol ester derivatives may alter the release of interleukin 2 (IL-2) in mammalian subjects. In an additional embodiment, compositions containing phorbol esters and/or phorbol ester derivatives may alter the release of interferon in mammalian subjects. In yet another embodiment, compositions containing phorbol esters and/or phorbol ester derivatives may alter the rate of ERK phosphorylation.

The invention achieves the foregoing and satisfies additional objects and advantages by providing novel and surprisingly unexpected methods and compositions useful for treating or reducing the duration of cytopenia, such as neutropenia, thrombocytopenia, and anemia.

DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
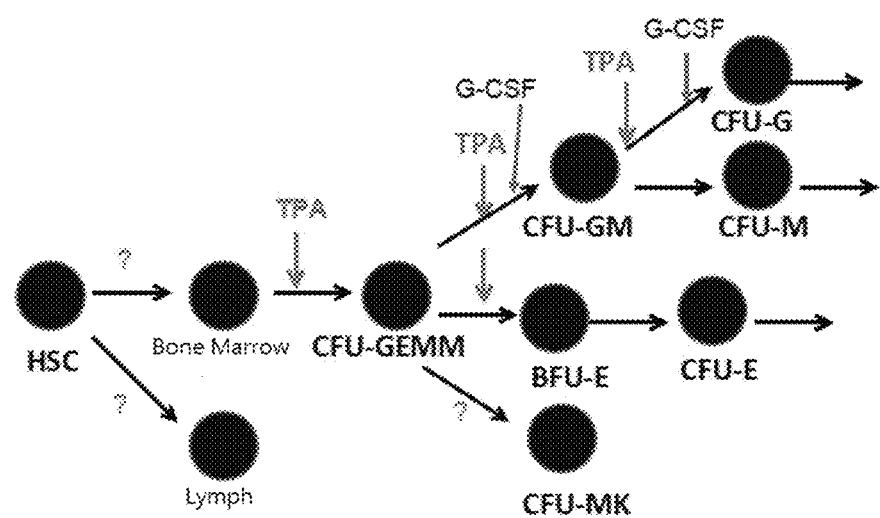
FIG. 1 illustrates the synergistic effect achieved by the combination of TPA and GCSF. TPA stimulates upstream stem cells to differentiate into downstream stem cells, while GCSF stimulates the downstream stem cells. TPA also stimulates downstream stem cells. Neutrophils are one type of granulocyte.

CFCs colony-forming cells
CFU-E colony forming unit-erythroid
CFU-G colony forming unit-granulocyte
CFU-GEMM colony forming unit-granulocyte, erythrocyte, macrophage, megakaryocyte
CFU-GM colony forming unit-granulocyte, macrophage
CFU-M colony forming unit-macrophage
BFU-E Burst forming unit erythroid The forgoing and additional objects, features, aspects and advantages of the present invention will become apparent from the following detailed description.

DETAILED DESCRIPTION OF THE INVENTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as would be understood by a person of ordinary skill in the art.

"G-CSF" or "GCSF" is known as granulocyte-colony stimulating factor or colony-stimulating factor 3 ("CSF3"), and may be used interchangeably herein. "G-CSF," "GCSF," or "CSF3" is a glycoprotein that stimulates the bone marrow to produce granulocytes and stem cells and release them into the bloodstream.

"EPO" is known as erythropoietin, which is a glycoprotein hormone that controls erythropoiesis, or red blood cell production.

Induction therapy is used herein to mean the first phase of treatment for a disease, typically, cancer. For example, the goal of induction therapy for acute myeloid leukemia is to produce a complete remission in the bone marrow and return to normal blood counts.

Consolidation therapy is used herein to mean treatment(s) given after cancer has disappeared following initial treatment, and is given to prevent recurrence of cancer. Consolidation therapy is used to kill any cancer cells that may be left in the body.

Cytopenia is used herein to mean a reduction in the number of blood cells, and includes low red blood cell count (anemia), low white blood cell count (leukopenia or neutropenia), low platelet count (thrombocytopenia), or a combination thereof (pancytopenia), and low granulocyte count (granulocytopenia).

Red blood cell count (RBC) is the number of red blood cells capable of carrying hemoglobin in a $mm^3$ of blood. The normal RBC for men is 4.5 to 6 million $mm^3$; for women, 4 to 5.5 million per $mm^3$. See cytopenia-cancertype-.blogspot.ca/2007/12/diagnosis-of-cytopenia.html.

White blood cell count (WBC) is the total number of all five types of white blood cells. The normal WBC for men and women is 5,000 to 10,000 per mm of blood. See cytopenia-cancertype.blogspot.ca/2007/12/diagnosis-of-cytopenia.html.

The articles "a" and "an" are used herein to refer to one or to more than one (i.e. to at least one) of the grammatical object of the article. By way of example, "an element" means one element or more than one element.

The terms "comprise" and "comprising" are used in the inclusive, open sense, meaning that additional elements may be included.

The term "consisting essentially of" is used to limit the elements to those specified and those that do not materially affect the basic and novel characteristics of the material or steps.

The term "including" is used herein to mean "including but not limited to." "Including" and "including but not limited to" are used interchangeably.

A "patient," "subject" or "host" to be treated by the subject method may mean either a mammal such as a human, or non-human mammal.

The term "pharmaceutically-acceptable carrier" is an art-recognized term and refers to a pharmaceutically-acceptable material, composition or vehicle, such as a liquid or solid filler, diluent, excipient, solvent or encapsulating material. Such carrier must be "acceptable" in the sense of being compatible with the subject composition and its components and not injurious to the patient. Examples include, but are not limited to, binders, fillers, lubricants, emulsifiers, suspending agents, sweeteners, flavorings, preservatives, buffers, wetting agents, disintegrants, effervescent agents and other conventional excipients and additives.

The term "treating" is an art-recognized term and refers to curing as well as ameliorating or reducing at least one symptom of any condition or disorder.

The term "therapeutic agent" or "drug" is an art-recognized and refers to any chemical moiety that is a biologically, physiologically, or pharmacologically active substance that acts locally or systemically in a subject. For example, therapeutic agents or drugs, are described in the Merck Index, the Physicians' Desk Reference, and The Pharmacological Basis of Therapeutics.

The term "effective amount" is therapeutically effective, in single or multiple unit dosage form. The effective amount is an amount that is sufficient to provide a therapeutic effect in a mammal, including a human. For example, an effective amount may be an amount sufficient to measurably treat or reduce/shorten the duration of neutropenia and/or thrombocytopenia in a subject. Another example of an effective amount is an amount sufficient to measurably treat or reduce/shorten the duration of anemia. Dosage levels or amounts of the particular therapeutic agent or drug used to provide a therapeutically effective amount vary depending on factors including, but not limited to, age, weight, gender, medical condition of the mammal/human, and the route of administration. Effective amounts of a phorbol ester compound or related or derivative compound of Formula I (e.g., a unit dose comprising an effective concentration/amount of TPA, or of a selected pharmaceutically acceptable salt, isomer, enantiomer, solvate, polymorph and/or prodrug of TPA), of G-CSF, or of EPO, will be readily determined by those of ordinary skill in the art, depending on clinical and patient-specific factors. A therapeutically effective amount according to the present invention may include a synergistically effective amount.

Cytopenia has traditionally been classified as a deficiency related (i.e., nutritional or hormonal deficiency), immune mediated, BM failure based, or idiopathic cytopenias. See Valent, P., Hematology: 485-491 (2012), the disclosure of which is herein incorporated by reference in its entirety.

Diagnosis of cytopenia in a cancer patient requires a complete blood count (CBC) and the identification of any blood and bone marrow abnormalities, such as anemia, neutropenia, or thrombocytopenia. See cytopenia-cancertype.blogspot.ca/2007/12/diagnosis-of-cytopenia.html.

Chemotherapeutic agents adversely affect bone marrow cells, and a complete blood count (CBC) is necessary prior to each treatment. The effects on bone marrow are temporary and normal functioning usually returns within 4-10 days, but white blood cells have a life span of 1 to 3 days; so although those WBCs in circulation remain unaffected, the slow production of new leukocytes creates a period of increased risk for infection. See cytopenia-cancertype.blogspot.ca/2007/12/diagnosis-of-cytopenia.html. If white blood cell production does not recover before the next treatment, treatment is delayed until the cell count increases sufficiently. Id. Mature red blood cells have a relatively long life (120 days), cell production usually resumes before symptoms of deficiency develop. Id.

Anemia is a deficiency in erythrocytes that reduces the amount of oxygen reaching all cells in the body, so that all tissue and organ function is impaired. Anemia produces symptoms including severe fatigue, confusion, dizziness, headache, lightheadedness, loss of concentration, pallor (pale skin, nail beds, gums, linings of eyelids), rapid heart rate (tachycardia), and shortness of breath (dyspnea). See cytopenia-cancertype.blogspot.ca/2007/12/cytopenia-signs-and-symptoms.html. Individuals with anemia are advised to rest and eat foods high in iron, and treatment may include medication that helps restore the red blood supply (such as erythropoietin) and a transfusion of packed red blood cells. See cytopenia-cancertype.blogspot.ca/2007/12/cytopenia-treatment.html. The Food and Drug Administration (FDA) in March 2007 issued a warning about these medications in response to studies indicating that they may increase the risk for blood clots, strokes, and heart attacks in some patients (e.g., patients who have kidney disease). Id.

Neutropenia is a white blood cell deficiency with symptoms including frequent and/or severe bacterial, viral, and/or fungal infections; fever; and mouth and throat ulcers. See cytopenia-cancertype.blogspot.ca/2007/12/cytopenia-signs-and-symptoms.html. A colony-stimulating factor (CSF), may be prescribed to speed the development of white blood cells and shorten the period of susceptibility to infection. See cytopenia-cancertype.blogspot.ca/2007/12/cytopenia-treatment.html.

Thrombocytopenia is a platelet deficiency that causes patients to bruise and bleed easily, and is characterized by symptoms including bleeding n the mucous membranes lining the mouth, nose, colon, and vagina. See cytopenia-cancertype.blogspot.ca/2007/12/cytopenia-signs-and-symptoms.html. It is characterized by a below normal platelet count of 15,000 to 300,000 per milliliter and the risk of increased bleeding usually peaks 10 to 14 days following a course of chemotherapy. Id. A persistently decreased platelet count may be treated with a transfusion of platelets. See cytopenia-cancertype.blogspot.ca/2007/12/cytopenia-treatment.html.

Growth factors (such as Epoetin alpha (Procrit®, Epogen®), G-CSF (granulocyte colony-stimulating factor; e.g., filgrastim [Neupogen®], and GM-CSF (granulocyte-macrophage colony-stimulating factor)) are synthetic versions of substances involved in stimulating red and white blood cell production, but caution is exercised when prescribing these medications for people with tumors that involve the bone marrow, because growth factors might stimulate malignant cell growth. See cytopenia-cancertype.blogspot.ca/2007/12/cytopenia-treatment.html. The side effects associated with these growth factors include fever, fatigue, dizziness, diarrhea, nausea, vomiting, weakness, and paresthesia (prickling sensation) (with epoetin alpha); and bone pain with (G-CSF). Id.

Chemotherapy and radiation therapy both reduce the number of blood-forming stem cells in cancer patients, but chemotherapeutic agents have a greater adverse effect because they suppress bone marrow function in several ways—the extent of damage is related to the particular drug(s) and the dose used. See cytopenia-cancertype.blogspot.ca/2007/12/cytopenia-causes-and-risk-factors.html.

Deficiencies in blood cell types can be caused by chemotherapeutic agents which damage blood-forming stem cells, suppress the kidneys' production of erythropoietin (hormone that stimulates blood cell production), and trigger red cell destruction (hemolysis) by inducing an immune response that causes the body to mistakenly identify erythrocytes as foreign bodies and destroy them. See cytopenia-cancertype.blogspot.ca/2007/12/cytopenia-causes-and-risk-factors.html. However, anemia, thrombocytopenia, and neutropenia caused by cancer treatment are usually resolved once the course of treatment is over. See cytopenia-cancertype.blogspot.ca/2007/12/cytopenia-treatment.html.

Malignant tumors can also cause anemia and other cytopenias when they directly invade bone marrow and suppress marrow function. See cytopenia-cancertype.blogspot.ca/2007/12/cytopenia-causes-and-risk-factors.html.

The compositions and methods as described herein may be used to treat or reduce/shorten the duration of anemia, neutropenia and/or thrombocytopenia in mammalian subjects, including humans. In some embodiment, the mammalian subject is a human with neoplastic disease.

Compositions and methods of using a phorbol ester of Formula I, below:

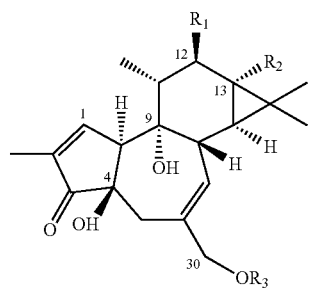

Formula I wherein $R_1$ and $R_2$ may be hydrogen; hydroxyl;

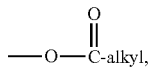

wherein the alkyl group contains 1 to 15 carbon atoms;

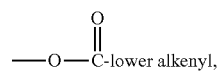

wherein a lower alkenyl group contains between 1 to 7 carbon atoms;

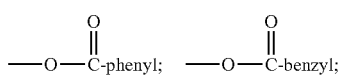

and substituted derivatives thereof. $R_3$ may be hydrogen or

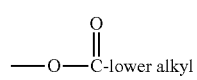

and substituted derivatives thereof; in combination with G-CSF for treatment of cytopenia including but not limited to, neutropenia and/or thrombocytopenia. The methods and compositions of the present invention further include any pharmaceutical salts, enantiomers, isomer, polymorphs, prodrugs, hydrates and solvates of the compositions of Formula I; in combination with G-CSF for treatment of neutropenia and/or thrombocytopenia. For example, the combination of phorbol ester of Formula I with G-CSF is also useful for reducing or shortening the duration of neutropenia and/or thrombocytopenia.

Compositions and methods of using a phorbol ester of Formula I, below:

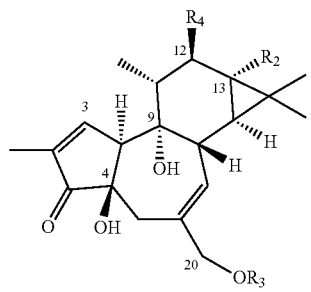

Formula I wherein $R_1$ and $R_2$ may be hydrogen; hydroxyl;

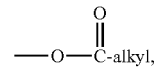

wherein the alkyl group contains 1 to 15 carbon atoms;

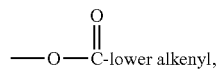

wherein a lower alkenyl group contains between 1 to 7 carbon atoms;

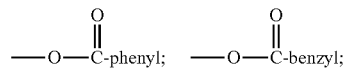

and substituted derivatives thereof. $R_3$ may be hydrogen or

and substituted derivatives thereof; in combination with EPO for treatment of cytopenia, including but not limited to, anemia. The methods and compositions of the present invention further include any pharmaceutical salts, enantiomers, isomer, polymorphs, prodrugs, hydrates and solvates of the compositions of Formula I; in combination with EPO for treatment of anemia. For example, the combination of phorbol ester of Formula I with EPO is also useful for reducing or shortening the duration of anemia.

In some embodiments, at least one of $R_1$ and $R_2$ are other than hydrogen and $R_3$ is hydrogen or

and substituted derivatives thereof. In another embodiment, either $R_1$ or $R_2$ is

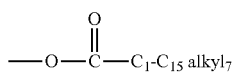

the remaining $R_1$ or $R_2$ is a

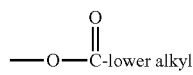

wherein a lower alkyl is between 1 and 7 carbons, and $R_3$ is hydrogen.

The alkyl, alkenyl, phenyl and benzyl groups of the formulas herein may be unsubstituted or substituted with halogens, preferably, chlorine, fluorine or bromine; nitro; amino; and/or similar type radicals.

Compositions and methods using the same include a combination of a phorbol ester of Formula II, as 12-O-tetradecanoylphorbol-13-acetate (TPA):

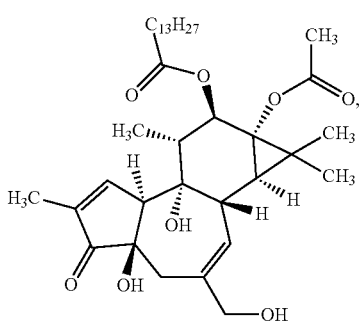

Formula II with G-CSF, for treatment of cytopenia, including but not limited to, neutropenia and/or thrombocytopenia. For example, the combination of TPA with G-CSF is also useful for reducing or shortening the duration of neutropenia and/or thrombocytopenia Compositions and methods using the same include a combination of a phorbol ester of Formula II, as 12-O-tetradecanoylphorbol-13-acetate (TPA):

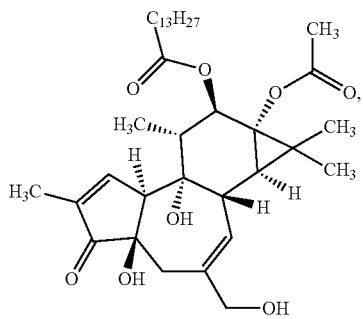

Formula II with EPO, for treating cytopenia, including but not limited to, anemia. For example, the combination of TPA with EPO is also useful for reducing or shortening the duration of anemia.

Useful phorbol esters of Formula I and related compounds and derivatives within the formulations and methods of the invention include, but are not limited to, other pharmaceutically acceptable active salts of said compounds, as well as active isomers, enantiomers, polymorphs, glycosylated derivatives, solvates, hydrates, and/or prodrugs of said compounds. Exemplary forms of phorbol esters for use within the compositions and methods of the invention include, but are not limited to, phorbol 13-butyrate; phorbol 12-decanoate; phorbol 13-decanoate; phorbol 12,13-diacetate; phorbol 13,20-diacetate; phorbol 12,13-dibenzoate; phorbol 12,13-dibutyrate; phorbol 12,13-didecanoate; phorbol 12,13-dihexanoate; phorbol 12,13-dipropionate; phorbol 12-myristate; phorbol 13-myristate; phorbol 12-myristate-13-acetate (also known as TPA or PMA); phorbol 12,13,20-triacetate; 12-deoxyphorbol 13-angelate; 12-deoxyphorbol 13-angelate 20-acetate; 12-deoxyphorbol 13-isobutyrate; 12-deoxyphorbol 13-isobutyrate-20-acetate; 12-deoxyphorbol 13-phenylacetate; 12-deoxyphorbol 13-phenylacetate 20-acetate; 12-deoxyphorbol 13-tetradecanoate; phorbol 12-tigliate 13-decanoate; 12-deoxyphorbol 13-acetate; phorbol 12-acetate; and phorbol 13-acetate.

A broad range of mammalian subjects, including human subjects, are amenable to treatment using the compositions and methods of the invention. These subjects include, but are not limited to, individuals suffering from diseases or conditions including but not limited to, neoplastic diseases, side effects from chemotherapy, side effects from radiation therapy, prostate hypertrophy, urinary incontinence, Myasthemia gravis, and kidney disease.

Mammalian subjects that are amenable to treatment with phorbol esters of Formula I, or derivative of the phorbol esters of the Formula I, particularly TPA, in combination with GCSF or EPO according to the methods of the present invention include subjects suffering from anemia, neutropenia and/or thrombocytopenia. Such subjects amenable to treatment with phorbol esters of Formula I, particularly TPA, in combination with GCSF or EPO include those suffering from symptoms of diseases or disorders including but not limited to, neoplastic diseases or effects caused by treatment of the neoplastic disease.

Additional mammalian subjects, including humans, amenable to treatment with compositions and methods as described herein, particularly TPA, according to the methods of the present invention include subjects or individuals with anemia related diseases or conditions, including but not limited to, anemia related to kidney failure or disease, anemia related to pregnancy, anemia related to poor nutrition, pernicious anemia, sickle cell anemia, thalassemia, alcoholism, bone marrow-related anemia (such as leukemia or lymphoma), aplastic anemia (from viral infections), anemia related to medications (such as cancer medications, HIV medications, seizure medications, transplant medications, malaria medications, antibiotics, antifungal, and antihistamines), hemolytic anemia, anemia related to thyroid problems, anemia related to liver disease, and autoimmune disease (such as lupus).

Additional mammalian subjects, including humans, amenable to treatment with compositions and methods as described herein, particularly TPA, according to the methods of the present invention include subjects or individuals with neutropenia related diseases or conditions, including but not limited to, congenital neutropenia (such as Kostmann's syndrome), cyclic neutropenia, idiopathic neutropenia, autoimmune neutropenia, and drug-induced neutropenia (such as from cancer drugs).

Additional mammalian subjects, including humans, amenable to treatment with compositions and methods as described herein, particularly TPA, according to the methods of the present invention include subjects or individuals with thrombocytopenia related diseases or conditions, including but not limited to, viral infections (such as parvovirus, rubella, mumps, varicella, hepatitis C, Epstein-Barr virus, and HIV), severe infections or sepsis, drug-induced thrombocytopenia (such as from cancer drugs, thiazide, sulfonamide antibiotics, carbamazepine, digoxin, quinine, quinidine, acetaminophen, heparin, and ripampin), transfusion reactions, rheumatologic conditions (such as systemic lupus erythematosus), and idiopathic thrombocytopenia purpura. These and other subjects are effectively treated prophylactically and/or therapeutically, by administering to the subject an effective amount of a phorbol ester of Formula I or derivative of a phorbol ester of Formula I sufficient to treat and/or reduce the duration of anemia, neutropenia and/or thrombocytopenia in mammalian subjects with a neoplastic disease.

Chemotherapy is the treatment of cancer with an antineoplastic drug or combination of such drugs. Chemotherapy works by impairing the reproduction of rapidly splitting cells, a property common in cancerous cells. However it does not actively distinguish between healthy cells that are also rapidly splitting and cancerous cells and it has a number of side effects such as, but not limited to, neutropenia, anemia, and thrombocytopenia.

Mammalian subjects amenable to treatment with phorbol esters of Formula I, particularly TPA, according to the methods of the present invention additionally include, but are not limited to, mammalian subjects undergoing chemotherapy.

Mammalian subjects suffering from neoplastic disease include malignant neoplastic diseases such as solid and non-solid cancers. Non-solid cancers may include, hematologic malignancies/bone marrow disorders, including, but not limited to, leukemia, including acute myeloid leukemia (AML), chronic myeloid leukemia (CML), chronic myeloid leukemia blast crisis, myelodysplasia, myeloproliferative syndrome. Solid cancers may include, but are not limited to, lymphoma, including Hodgkin's and non-Hodgkin's lymphoma, subcutaneous adenocarcinoma, ovarian teratocarcinoma, lung cancer; bone cancer; breast cancer; liver cancer; pancreatic cancer; oral cancer; non-small cell lung cancer and prostate cancer.

Therapeutically useful methods and formulations of the invention will effectively use a phorbol ester of Formula I in a variety of forms, as noted above, including any active, pharmaceutically acceptable salts of said compounds, as well as active isomers, enantiomers, polymorphs, solvates, hydrates, prodrugs, and/or combinations thereof. TPA of formula II is employed as an illustrative embodiment of the invention within the examples herein below.

Within additional aspects of the invention, combinatorial formulations and methods are provided which employ an effective amount of a phorbol ester of Formula I or derivative of a phorbol ester of Formula I in combination with one or more secondary or adjunctive active agent(s) that is/are combinatorially formulated or coordinately administered with the phorbol ester compound of Formula I to yield an effective response in the subject.

A phorbol ester compound of Formula I or derivative of the phorbol ester of Formula I is used in combination with G-CSF. Specifically, G-CSF is used in combination with a phorbol ester, e.g., TPA.

A phorbol ester compound of Formula I or derivative of the phorbol ester of Formula I is used in combination with erythropoeitin (EPO). Specifically, EPO is used in combination with TPA.

A phorbol ester compound of Formula I or derivative of the phorbol ester of Formula I is used in combination with G-CSF. Specifically, G-CSF is used in combination with TPA.

Compositions as described herein comprise G-CSF and a phorbol ester compound of Formula I or derivative compound of phorbol esters of Formula I including pharmaceutically acceptable salts, enantiomers, isomers, polymorphs, prodrugs, hydrates and solvates thereof, in an effective amount to treat or reduce the duration of neutropenia and/or thrombocytopenia.

Compositions as described herein comprise EPO and a phorbol ester compound of Formula I or derivative compound of phorbol esters of Formula I including pharmaceutically acceptable salts, enantiomers, isomers, polymorphs, prodrugs, hydrates and solvates thereof, in an effective amount to treat or reduce the duration of anemia.

The compositions of the invention comprise G-CSF and a phorbol ester compound of Formula I or derivative compound of phorbol esters of Formula I including pharmaceutically acceptable salts, enantiomers, isomers, polymorphs, prodrugs, hydrates and solvates thereof, in a synergistically effective amount or synergistic combination effective to treat or reduce the duration of neutropenia and/or thrombocytopenia. The compositions of the invention are synergistically effective in treating or reducing the duration of neutropenia and/or thrombocytopenia in human and other mammalian subjects with neoplastic disease. A "synergistically effective amount" as applied to compositions of the invention comprise G-CSF and a phorbol ester compound of Formula I or derivative compound of phorbol esters of Formula I including pharmaceutically acceptable salts, enantiomers, isomers, polymorphs, prodrugs, hydrates and solvates thereof, is effective for shortening the duration of neutropenia and/or thrombocytopenia, which is effective in treating or reducing the duration of neutropenia and/or thrombocytopenia. The effect produced by the combination of the present invention results in a response greater than G-CSF or a phorbol ester compound of Formula I or derivative compound of phorbol esters of Formula I, alone or the sum of their individual effects A synergistically effective amount of a phorbol ester of Formula I (such as TPA) with G-CSF or a synergistically effective amount of a combination of a phorbol ester of Formula I (such as TPA) with EPO, may be administered to a mammal in a single or multiple unit form either simultaneously or sequentially, in combined or separate formulation(s), with one or more secondary agents, or one or more adjunctive therapeutic agents; by an oral method (such as capsules, in liquid form, tablets, etc.), parenteral method (such as parenteral injection), or by any other methods known in the art suitable for administering drugs to mammals.

The compositions of the invention comprise EPO and a phorbol ester compound of Formula I or derivative compound of phorbol esters of Formula I including pharmaceutically acceptable salts, enantiomers, isomers, polymorphs, prodrugs, hydrates and solvates thereof, in a synergistically effective amount or synergistic combination effective to treat or reduce the duration of anemia. In particular, the compositions of the invention are synergistically effective in treating or reducing the duration of anemia in human or other mammalian subjects with neoplastic disease.

The compositions of the invention comprise an effective amount or unit dosage of a phorbol ester compound of Formula I or derivative compound of a phorbol ester of Formula I, and G-CSF which may be formulated with one or more pharmaceutically acceptable carriers, excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use.

Effectiveness of the compositions and methods of the invention may be demonstrated by a decrease in the duration of anemia, neutropenia and/or thrombocytopenia.

Compositions of the invention may be coordinately administered (simultaneously or sequentially, in combined or separate formulation(s)), with one or more secondary cancer treating agents, or other indicated or adjunctive therapeutic agents, including, but not limited to, doxorubicin, vitamin D3, cytarabine, cytosine arabinoside, daunorubicin, cyclophosphamide, gemtuzumab ozogamicin, idarubicin, mercaptopurine, mitoxantrone, thioguanine, aldesleukin, asparaginase, carboplatin, etoposide phosphate, fludarabine, methotrexate, etoposide, dexamethasone, and choline magnesium trisalicylate.

Within the methods and compositions of the invention, a phorbol ester compound(s) of Formula I (such as TPA) as disclosed herein is/are effectively formulated or administered with GCSF for treating neutropenia, thrombcytopenia and/or related disorders. In exemplary embodiments, TPA is demonstrated for illustrative purposes to be an effective agent in pharmaceutical formulations and therapeutic methods, in combination with GCSF. The present disclosure further provides additional, pharmaceutically acceptable phorbol ester compounds (such as TPA) in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention.

Compositions of the invention may comprise a phorbol ester compound of Formula I (such as TPA) encapsulated for delivery, separately or together with GCSF or EPO, in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively; in colloidal drug delivery systems (for example, liposomes, albumin microspheres, microemulsions, nano-particles and nanocapsules); or within macroemulsions.

As noted above, in certain embodiments the methods and compositions of the invention may employ pharmaceutically acceptable salts, e.g., acid addition or base salts of the above-described phorbol ester compounds of Formula I and/or related or derivative compounds (such as TPA). Examples of pharmaceutically acceptable addition salts include inorganic and organic acid addition salts. Suitable acid addition salts are formed from acids which form non-toxic salts, for example, hydrochloride, hydrobromide, hydroiodide, sulphate, hydrogen sulphate, nitrate, phosphate, and hydrogen phosphate salts. Additional pharmaceutically acceptable salts include, but are not limited to, metal salts such as sodium salts, potassium salts, cesium salts and the like; alkaline earth metals such as calcium salts, magnesium salts and the like; organic amine salts such as triethylamine salts, pyridine salts, picoline salts, ethanolamine salts, triethanolamine salts, dicyclohexylamine salts, N,N'-dibenzylethylenediamine salts and the like; organic acid salts such as acetate, citrate, lactate, succinate, tartrate, maleate, fumarate, mandelate, acetate, dichloroacetate, trifluoroacetate, oxalate, and formate salts; sulfonates such as methanesulfonate, benzenesulfonate, and p-toluenesulfonate salts; and amino acid salts such as arginate, asparginate, glutamate, tartrate, and gluconate salts. Suitable base salts are formed from bases that form non-toxic salts, for example aluminum, calcium, lithium, magnesium, potassium, sodium, zinc and diethanolamine salts.

Other detailed embodiments, the methods and compositions of the invention for employ prodrugs of phorbol esters of Formula I. Prodrugs are considered to be any covalently bonded carriers which release the active parent drug in vivo. Examples of prodrugs useful within the invention include esters or amides with hydroxyalkyl or aminoalkyl as a substituent, and these may be prepared by reacting such compounds as described above with anhydrides such as succinic anhydride.

For instance, in current AML therapeutic regimen, G-CSF has been a common adjuvant drug for reducing the duration of neutropenia, but not thrombocytopenia, after chemotherapy. The present invention indicates that G-CSF combined with phorbol esters such as TPA can treat or reduce the duration of both neutropenia and/or thrombocytopenia through the following two mechanisms.
1) TPA stimulates the upstream stem cells to differentiate into downstream stem cells. TPA also stimulates downstream stem cells. GCSF only stimulates the downstream stem cells.
2) TPA stimulates the growth of stromal cells, which nourish the stem cells.

For example, the duration of neutropenia after high dose chemotherapy and treatment with GCSF is, for example, about 24±3 days. The combination of TPA and GCSF reduces the duration of neutropenia to about 15±3 days, or about a 25% to 50% reduction in the duration of neutropenia.

The combination of TPA and GCSF may result in about a 15% to 70% reduction in the duration of cytopenia, including but not limited to, neutropenia, thrombocytopenia, and/or anemia in comparison to treatment with GCSF or TPA alone. More preferably, the combination results in about at 20% to 60% reduction in the duration of cytopenia; and most preferably, the combination results in about a 25% to 50% reduction in the duration of cytopenia.

Likewise, the combination of TPA and EPO may result in about a 15% to 70% reduction in the duration of cytopenia, including but not limited to, neutropenia, thrombocytopenia, and/or anemia in comparison to treatment with EPO or TPA alone. More preferably, the combination results in about at 20% to 60% reduction in the duration of cytopenia; and most preferably, the combination results in about a 25% to 50% reduction in the duration of cytopenia.

The invention achieves a surprisingly synergistic effect by stimulating upstream stem cells to differentiate into downstream stem cells, as shown in FIG. 1.

Alternatively, effectiveness of the compositions and methods of the invention may also be demonstrated, for example, by an increase toward normal levels of red blood cells, white blood cells, neutrophils, and/or platelets. For instance, effectiveness of the compositions and methods of the invention may be demonstrated by a decrease in neutropenia, anemia, and/or thrombocytopenia.

Effectiveness may be demonstrated using, for example, a complete blood count (CBC). The measurements taken in a CBC include a white blood cell count (WBC), a red blood cell count (RBC), the red cell distribution width, the hematocrit, and the amount of hemoglobin. An effective amount of a composition of the present invention will increase the levels measured in a complete blood count by 10%, 20%, 30%, 50% or greater increase, up to a 75-90%, or 95% or greater. Effective amounts will also move the blood protein of an individual towards the optimal category for each type of protein.

A normal erythrocyte (RBC) count is from $4.0 \times 10^{12}/l$ to $5.2 \times \times 10^{12}/l$ (in females) and from $4.4 \times 10^{12}/l$ to $5.7 \times 10^{12}/l$ (in males). Effectiveness of the compositions and methods herein will increase the RBC count towards the normal count range.

A normal hemoglobin level is typically from 130 g/l to 175 g/l. Specifically, the normal hemoglobin level is typically from 140 g/l to 180 g/l in human males, and the normal hemoglobin level is typically from 120 g/l to 160 g/l in human females. Anemia is a decrease in the amount of RBCs or hemoglobin in the blood. Anemia in men is based on a hemoglobin of less than 130 to 140 g/L (13 to 14 g/dL), while anemia in women is less than 120 to 130 g/L (12 to 13 g/dL). Effectiveness of the compositions and methods herein will increase the hemoglobin level towards the normal hemoglobin level.

A normal hematocrit level is from 0.370 to 0.460 (in females) and is from 0.420 to 0.520 (in males). Effectiveness of the compositions and methods herein will increase the hematocrit level towards the normal range.

A normal WBC count is from $4.0 \times 10^9/l$ to $10.0 \times \times 10^9/l$. Effectiveness of the compositions and methods herein will increase the WBC count towards the normal count range.

Effectiveness of the compositions and methods herein may be evaluated using, an absolute neutrophil count (ANC). A normal ANC is between 1,500 to 8,000/mm$^3$. Individuals suffering from neutropenia have an ANC below 1500/mm$^3$, and may even reach levels below 500/mm$^3$. Effective amounts of the compositions and methods herein will increase an individual's ANC by 10%, 20%, 30%, 50% or greater increase, up to a 75-90%, or 95% or greater. Effective amounts may increase ANC levels above 1500/mm$^3$.

Effectiveness of the compositions and methods herein may further be evaluated using, for example, a platelet count. A platelet count is normally between 150,000 to 450,000 platelets per microliter (×10-6/Liter). Individuals suffering from thrombocytopenia may have platelet counts below 100,000 per microliter (100,000/μl). Effective amounts of the compositions and methods herein will increase an individual's platelet count by 10%, 20%, 30%, 50% or greater increase, up to a 75-90%, or 95% or greater. Effective amounts may increase platelet levels above 100,000 per microliter.

Effectiveness of the compositions and methods herein may additionally be evaluated, for example, by measuring the number of myeloblasts. Myeloblasts normally represent less than 5% of the cells in the bone marrow but should not be present in circulating blood. Effective amounts of the compositions and methods herein will decrease the number of myeloblasts by 10%, 20%, 30%, 50% or more, up to a 75-90%, 96% or greater decrease. Effective amounts may decrease myeloblasts to below 5%.

Effectiveness of the compositions and methods herein may further be evaluated by examining myeloblasts for the presence of Auer rods. Effective amounts of the compositions of the present invention will decrease the number of Auer rods visible by 10%, 20%, 30%, 50% or more, up to a 75-90%, 96% or greater decrease up to the complete elimination of Auer rods.

Effectiveness of the compositions and methods of the invention may be demonstrated by a decrease in the symptoms that accompany cytopenia, including but not limited to, neutropenia, anemia, and/or thrombocytopenia.

Effective amounts of a phorbol ester compound or related or derivative compound of Formula I (e.g., a unit dose comprising an effective concentration/amount of TPA, or of a selected pharmaceutically acceptable salt, isomer, enantiomer, solvate, polymorph and/or prodrug of TPA) will be readily determined by those of ordinary skill in the art, depending on clinical and patient-specific factors. Suitable effective unit dosage amounts of the active compounds for administration to mammalian subjects, including humans, may range from about 10 to about 1500 μg, about 20 to about 1000 μg, about 25 to about 750 μg, about 50 to about 500 μg, about 150 to about 500 μg, about 125 μg to about 500 μg, about 180 to about 500 μg, about 190 to about 500 μg, about 220 to about 500 μg, about 240 to about 500 μg, about 260 to about 500 μg, about 290 to about 500 μg. In certain embodiments, the disease treating effective dosage of a phorbol ester compound or related or derivative compound of Formula I may be selected within narrower ranges of, for example, 10 to 25 μg, 30-50 μg, 75 to 100 μg, 100 to 300 μg, or 150 to 500 μg. These and other effective unit dosage amounts may be administered in a single dose, or in the form of multiple daily, weekly or monthly doses, for example in a dosing regimen comprising from 1 to 5, or 2 to 3, doses administered per day, per week, or per month. In one exemplary embodiment, dosages of 10 to 30 μg, 30 to 50 μg, 50 to 100 μg, 100 to 300 μg, or 300 to 500 μg, are administered one, two, three, four, or five times per day. In more detailed embodiments, dosages of 50-100 μg, 100-300 μg, 300-400 μg, or 400-600 μg are administered once or twice daily. In a further embodiment, dosages of 50-100 μg, 100-300 μg, 300-400 μg, or 400-600 μg are administered every other day. In alternate embodiments, dosages are calculated based on body weight, and may be administered, for example, in amounts from about 0.5 μg/m$^2$ to about 300 μg/m$^2$ per day, about 1 μg/m$^2$ to about 200 μg/m$^2$, about 1 μg/m$^2$ to about 187.5 μg/m$^2$ per day, about 1 μg/m$^2$ per day to about 175 μg/m$^2$ per day, about 1 μg/m$^2$ per day to about 157 μg/m$^2$ per day about 1 μg/m$^2$ to about 125 μg/m$^2$ per day, about 1 μg/m$^2$ to about 75 μg/m$^2$ per day, 1 μg/m$^2$ to about 50/μg/m$^2$ per day, 2 μg/m$^2$ to about 50 μg/m$^2$ per day, 2 μg/m$^2$ to about 30 μg/m$^2$ per day or 3 μg/m$^2$ to about 30 μg/m$^2$ per day.

In other embodiments, dosages may be administered less frequently, for example, 0.5 μg/m$^2$ to about 300 μg/m$^2$ every other day, about 1 μg/m² to about 200 μg/m², about 1 μg/m² to about 187.5 μg/m² every other day, about 1 μg/m² to about 175 μg/m² every other day, about 1 μg/m² per day to about 157 μg/m² every other day about 1 μg/m² to about 125 μg/m² every other day, about 1 μg/m² to about 75 μg/m² every other day, 1 μg/m² to about 50 μg/m² every other day, 2 μg/m² to about 50 μg/m² every other day, 2 μg/m² to about 30 μg/m² per day or 3 μg/m² to about 30 μg/m² per day. In additional embodiments, dosages may be administered 3 times/week, 4 times/week, 5 times/week, only on weekdays, only in concert with other treatment regimens, on consecutive days, or in any appropriate dosage regimen depending on clinical and patient-specific factors.

Erythropoietin is a glycosylated protein hormone and a haematopoietic growth factor produced primarily in the kidneys, and for clinical use, is produced by recombinant DNA technology and the name epoetin is often applied to such material. See noblood.org/forum/content/179-erythropoietin_-28epo-29. Epoetin alfa, epoetin beta, epoetin gamma, epoetin omega, and epoetin zeta are recombinant human erythropoietins derived from a cloned human erythropoietin gene; all of which have the same 165 amino acid sequence but differ in the glycosylation pattern. Id. Epoetin delta is a recombinant human erythropoietin derived from a genetically engineered continuous human cell line, and has the same amino acid sequence and glycosylation pattern as human erythropoietin. Id.

EPO such as EPOETIN® may be given either as an IV or SC injection, as described at inceptapharma[dot]com/epoetin/submenu_page_view.php?menu_id=86&submenu_id=223&fs, the disclosure of which is herein incorporated by reference in its entirety. For instance, the dosage may be adjusted for each patient to achieve and maintain hemoglobin levels between 10 to 12 g/dL. Id. For example, if hemoglobin is increasing and approaching 12 g/dL, the dose may be reduced by approximately 25%; if the hemoglobin continues to increase, the dose may be temporarily withheld until the hemoglobin begins to decrease and then reinitiated at a dose approximately 25% below the previous dose; or if the hemoglobin increases by more than 1 g/dL in a 2-week period, the dose may be decreased by approximately 25%. Id. If the increase in the hemoglobin is less than 1 g/dL over 4 weeks and iron stores are adequate, the dose of EPOETIN® may be increased by approximately 25% of the previous dose. Further increases may be made at 4-week intervals until the specified hemoglobin is obtained. Id.

The dose of EPO may be titrated for each patient on chemotherapy or who have undergone chemotherapy, to achieve and maintain the lowest hemoglobin level sufficient to avoid the need for blood transfusion and not to exceed the upper safety limit of 12 g/dL. inceptapharma[dot]com/epoetin/submenu_page_view.php?menu_id=86&submenu_id=223&fs The initial recommended dose of EPO in adults is 150 Units/kg SC TIW or 40,000 Units SC Weekly, and the initial recommended dose of EPO in pediatric patients is 600 Units/kg IV weekly. Id.

Suitable effective unit dosage amounts of erythropoeitin may depend on several factors and will be within the discretion of the subject's physician. For example, some patients may be more or less sensitive to the compounds or compositions described herein, and for those patients compositions providing a higher of a lower plasma or serum value may be preferred. Also, some subjects may metabolize the compound or may metabolize it at different rates, and so dosages and/or alternative dosage forms may be required to provide the desired serum or plasma concentration. Skilled artisans will appreciate that specific dosages of EPO in compositions of the present invention may be adjusted depending on conditions of disease, the age, body weight, general health conditions, sex, and diet of the subject, dose intervals, administration routes, excretion rate, and combinations of active compounds.

The dosing regimen for EPO may include doses such as 75 to 150 IU for every kilogram (u/kg) of body weight given daily or every other day; 600 u/kg given once a week; or 300 u/kg three or four times a week; as described at noblood.org/forum/content/179-erythropoietin_-28epo-29 is a suggested dosing guide, the disclosure of which is herein incorporated by reference in its entirety. For instance, for a 70 kg patient, 60,000 IU per week may be ordered. Id.

Suitable effective unit dosage amounts of EPO may include a range from 450 IU/kg to 900 IU/kg, given daily or every other day, or given once, twice, three times or four times a week. See, noblood.org/forum/content/179-erythropoietin_-28epo-29

Suitable effective unit dosage amounts of EPO-beta may include 1000 IU/0.3 mL, 2000 IU/0.3 mL, 3000 IU/0.3 mL, 4000 IU/0.3 mL, 5000 IU/0.3 mL, 6000 IU/0.3 mL, 10,000 IU/0.6 mL, and 30,000 IU/0.6 mL solutions; and contains urea, sodium chloride, sodium phosphate, and water, in pre-filled syringes for injection. See noblood.org/forum/content/179-erythropoietin_-28epo-29.

Epoetin alfa may be administered by injection of 1 mL of a water-based solution which may contain a single dose of 2000, 3000, 4000, 10,000, or 40,000 units of epoetin alfa per single dose, along with other ingredients including albumin, based on treatment requirements and weight of patient. See noblood.org/forum/content/179-erythropoietin_-28epo-29.

In addition, multidose injections may also be administered with 10,000 units or 20,000 units per 1 mL of injection solution. Id. This applies to other forms of EPO. Id. Chronic diseases, such as renal failure, heart disease, diabetes, and inflammatory diseases like rheumatoid arthritis, all contribute to anemia and produce a blunted response to EPO therapy—in all such cases the dosage should be increased. Id.

Dosages of EPO alfa (rch) or EPREX® may be administered as described at medsafe.govt.nz/profs/datasheet/e/eprexinj.pdf, the disclosure of which is herein incorporated by reference in its entirety. For example, EPO alfa may be administered subcutaneously with 150 units/kg 3 times weekly, or 40,000 units weekly, and/or 300 units/kg 3 times weekly or 60,000 units weekly. See drugs.com/ppa/epoetin-alfa-erythropoietin-epo.html, the disclosure of which is herein incorporated by reference in its entirety.

The dosage of EPO may include high doses as described in U.S. Pat. No. 7,232,797, the disclosure of which is herein incorporated by reference. For instance, U.S. Pat. No. 7,232,797 describes a dosage of EPO of 5000 IU/kg weekly or 17,000~25,000 IU/kg (biweekly or triweekly).

The dosage of EPO may include low doses as described in CA2418531, the disclosure of which is herein incorporated by reference. For instance, the CA2418531 patent describes dosage of EPO from about 1 to about 90 IU/kg per week; as well as an initial treatment dose of about 75 to about 120 IU/Kg per week and maintenance dose of about 20 to about 75 IU/Kg per week. In addition, CA2418531 describes administration of recombinant Epoetin Omega at a dose of 5-150 IU/Kg, one to three times per week.

An effective dose or multi-dose treatment regimen for the instant disease treating (alternatively, "neutrophil stimulating," "erythropoiesis stimulating," or "platelet stimulating")

formulations of the invention will ordinarily be selected to approximate a minimal dosing regimen that is necessary and sufficient to substantially treat or reduce/shorten the duration of anemia, neutropenia, and/or thrombocytopenia in the subject. A dosage and administration protocol will often include repeated dosing therapy over a course of several days or even one or more weeks or years. An effective treatment regime may also involve prophylactic dosage administered on a day or multi-dose per day basis lasting over the course of days, weeks, months or even years.

Effectiveness of the compositions and methods of the invention may also be demonstrated by a decrease in the symptoms of subjects suffering from neoplastic disease including, but not limited to, anemia, chronic fatigue; excessive or easy bleeding, such as bleeding of the nose, gums, and under the skin; easy bruising, particularly bruising with no apparent cause; shortness of breath; petechiae; recurrent fever; swollen gums; slow healing of cuts; bone and joint discomfort; recurrent infections; weight loss; itching; night sweats; lymph node swelling; fever; abdominal pain and discomfort; disturbances in vision; coughing; loss of appetite; pain in the chest; difficulty swallowing; swelling of the face, neck and upper extremities; a need to urinate frequently, especially at night; difficulty starting urination or holding back urine; weak or interrupted flow of urine; painful or burning urination; difficulty in having an erection; painful ejaculation; blood in urine or semen; frequent pain or stiffness in the lower back, hips, or upper thighs; and/or weakness.

Effectiveness of the compositions and methods of the invention in the treatment of rheumatoid arthritis may also be demonstrated by a change in the erythrocyte sedimentation rate. An effective amount of the compositions of the invention would decrease the levels of erythrocyte sedimentation by 10%, 20%, 30%, 50% or more, up to a 75-90%, 96% or greater decrease over the initial diagnostic levels of erythrocyte sedimentation. Effectiveness may also be demonstrated by a change in the levels of rheumatoid factor and anti-cyclic citrullinated antibodies.

The compounds and compositions described herein can be formulated into pharmaceutically acceptable compositions, which may include one or more pharmaceutically acceptable carriers. Such compositions may be prepared by mixing one or more compounds or compositions described herein, including, e.g., pharmaceutically acceptable salts thereof or stereoisomers thereof, with pharmaceutically acceptable carriers, excipients, binders, diluents or the like to treat or reduce the duration of cytopenia such as neutropenia, thrombocytopenia, and/or anemia.

The instant compositions can be formulated for various routes of administration, for example, by oral, transdermal, parenteral, rectal, nasal, vaginal administration, or via implanted reservoir or other device such as a stent. Such implants may employ known inert materials such as silicones and biodegradable polymers. They also may be provided in combination with delivery vehicles such as in micelles or liposomes, or some other encapsulating technology. Parenteral or systemic administration includes, but is not limited to, subcutaneous, intravenous, intraperitoneally, intramuscular, intrathecal, intracranial, and intracerebroventricular injections.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive, including but not limited to, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers and glycerides. Optionally, oral dosage forms can contain other ingredients to aid in administration, such as an inactive diluent, lubricants such as magnesium stearate, preservatives such as paraben or sorbic acid, anti-oxidants such as ascorbic acid, tocopherol or cysteine, a disintegrating agent, binders, thickeners, buffers, sweeteners, flavoring agents or perfuming agents. Tablets and pills may be further coated with coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, including, but not limited to, oil, water, alcohol, and combinations thereof. Pharmaceutically suitable surfactants, suspending agents, emulsifying agents, may be added for oral or parenteral administration.

Injectable dosage forms include aqueous suspensions or oil suspensions which may be prepared using a suitable dispersant or wetting agent and a suspending agent. Injectable forms may be in solution phase or in the form of a suspension, which is prepared with a solvent or diluent, including but is not limited to, sterilized water, Ringer's solution, or an isotonic aqueous saline solution. For injection, the pharmaceutical formulation and/or medicament may be a powder suitable for reconstitution with an appropriate solution, and may optionally contain stabilizers, pH modifiers, surfactants, bioavailability modifiers and combinations thereof. Examples of such suitable powders include, but are not limited to, freeze dried, rotary dried or spray dried powders, amorphous powders, granules, precipitates, or particulates.

Compounds and compositions described herein also may be administered to the lungs by inhalation through the nose or mouth. Suitable pharmaceutical formulations for inhalation include but are not limited to, aqueous and nonaqueous aerosols, solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations thereof. Formulations for inhalation administration may contain excipients including but not limited to, lactose, polyoxyethylene-9-lauryl ether, glycocholate and deoxycholate. An aqueous aerosol is made by formulating an aqueous solution or suspension of the compound or composition together with conventional pharmaceutically acceptable carriers and stabilizers, which include but are not limited to, nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols may be prepared from isotonic solutions, or a nonaqueous suspension (e.g., in a fluorocarbon propellant) can also be used to deliver embodiments of the compounds and compositions described herein.

The compounds and compositions of the present invention may be provided in a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations thereof, for nasal administration.

Compounds and compositions of the present invention may be provided for sustained or immediate release. Sustained release dosage forms control the rate of release, and can maintain an effective concentration of the composition over time, thereby providing the recipient with a therapeutic effect over an extended duration. The pharmaceutical composition is a dosage form selected from the group consisting of a tablet, liquid for oral administration, oral spray, intranasal spray, inhalable formulation, pill, gel, solid, capsule, multi-particulate, transdermal patch, implantable dosage, and injectable solution including intravenous drip (including in lyophilized and re-constituted form); as well as dosage forms that swell or unfold so that the dosage form is retained in the stomach or the upper portion of the small intestine for at period of least 1 hour, at least 2 hours, at least three hours, at least 4 hours, at least 5 hours, at least 6 hours or for a period of longer than 6 hours. Examples of patents that describe sustained release compositions include, but are not limited to, U.S. Pat. Nos. 7,438,927, 7,413,751, 7,405,238, 6,723,340, 6,682,759, 6,635,280, 6,488,962, 6,451,808, 6,340,475, 5,972,389, 5,582,837, and 5,007,790.

The following non-limiting examples are provided merely to illustrate various aspects or embodiments of the present invention.

EXAMPLES

Example 1

In Vitro Study of TPA and GCSF on Colony Forming Cells

Figure 2:
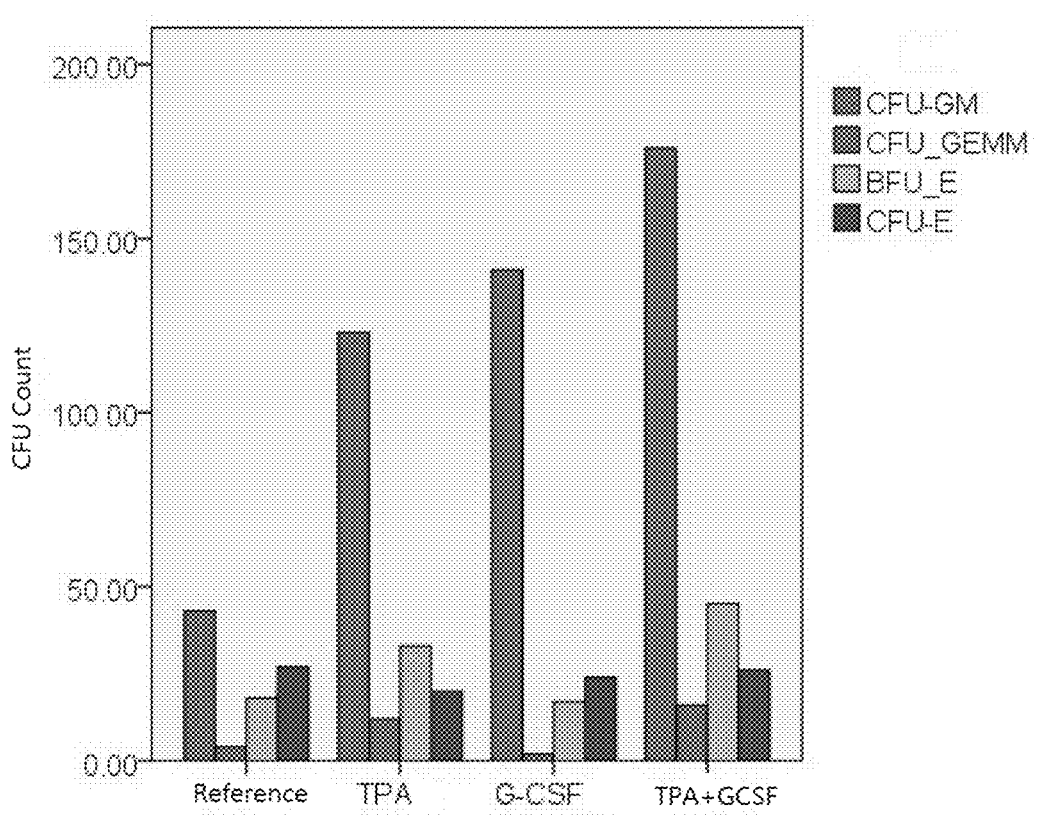
FIG. 2 illustrates the combination of TPA and GCSF generates stronger stimulating effects than TPA or G-CSF alone. The below abbreviations are used in FIG. 2 and throughout the present disclosure with respect to the following terminology.

The combination of TPA and GCSF generated stronger stimulating effects on colony forming cells than TPA or G-CSF alone, as shown in FIG. 2.

Myelosuppression is the most common adverse reactions of cancer patients who use chemotherapy drugs, severe bone marrow suppression often makes chemotherapy difficult to continue as planned, may be bring out the complications, could be life-threatening. Recently, rhG-CSF, EPO are used widely to treat leukopenia or anemia which coursed by chemotherapy and radiotherapy. But only rhG-CSF, EPO can not recover medullary hematopoiesis in the short term for those who accepted high intensity or many times chemotherapy, especially for leukemia patients. Because chemotherapy drugs can hurt the normal hematopoietic cells and microenvironment in the bone marrow, when they are killing cancer cells. Meanwhile rhG-CSF, EPO play a role in the downstream of hematopoiesis. Such as G-CSF effects on myeloid progenitor stage, which stimulate their proliferation, differentiation and promote mature neutrophils to be released into the peripheral blood. EPO play a role on erythroid progenitor cells stage, to stimulate erythropoiesis, increase the number of red blood cells in peripheral blood. But they have no effects on bone marrow microenvironment all. Therefore, it is important to find a way to quickly restore bone marrow hematopoiesis. It is reported that 12-O-tetradecanoylphorbol-13-acetate which is called phorbol ester (TPA), not only can induce a variety of leukemia cells to normal cells, but also TPA have a certain influence on bone marrow hematopoietic and can increase white blood cell.

To explore the effect of TPA alone or combined rhG-CSF on bone marrow hematopoietic cells proliferation and colony formation ability which from patients of acute myeloid leukemia (AML) in the period of bone marrow suppression in vitro and to observe the effect of TPA on bone marrow stromal cells (BMSCs) proliferation or inhibition from patients of AML in the period of myelosuppression and the healthy persons.

Methods:
1) Human bone marrow cells from the same AML patient after chemotherapy were cultured by methyl cellulose semi-solid culture medium. Groups: Blank, TPA (10 ng/ml), G-CSF (50 ng/ml), TPA (10 ng/ml)+GCSF (50 ng/ml). The experiments were repeated for 4 times.
2) The stroma cells of bone marrow from the healthy human and the AML patient after chemotherapy were cultured by methyl cellulose semi-solid culture medium. Different TPA concentrations were added. Groups: Blank, TPA (0.1 ng/ml), TPA (1.0 ng/ml), TPA (5 ng/ml), TPA (10 ng/ml), TPA (20 ng/ml), TPA (30 ng/ml).
3) Cultivation of BMSCs from healthy persons and patients of AML in the bone marrow suppression phase in vitro, added to TPA of different concentrations, 0.1 ng/ml, 1.0 ng/ml, 5 ng/ml, 10 ng/ml, 20 ng/ml, 30 ng/ml, and set up a control to detect cell proliferation or inhibition with CCK8 method.

Results and Conclusion:
1. Compared the clones of four groups in incomplete medium, in the control group a small cell clusters can be seen for 24-72 hours, but the cells were dead as time prolong. Cultivated 14 days, control group have no clones formation, CFU-GM are dominated for G-CSF group, TPA alone and combination with G-CSF group have myeloid colony formation, while BFU-E and CFU-GEMM. For G-CSF group, TPA alone group and combination with G-CSF group, the total number of clones were higher than control group (both $P<0.05$), meanwhile the clones for TPA alone group and combination with G-CSF group are higher than G-CSF group (both $P<0.05$), the clones of joint group is higher than that of TPA group ($P<0.001$).

2. Compared the clones of different concentration of TPA stimulation in incomplete medium, the total clones of 5 ng/ml, 10 ng/ml, 20 ng/ml group are higher than other groups, including 10 ng/ml in the highest, there are statistical significance (both $P<0.05$). While decreasing or increasing TPA concentration can not improve the colony number. The better concentration of TPA to stimulate the colony formation is 5~20 ng/ml. Cultivated 14 days, except CFU-GM, CFU-GEMM were seen in 1 ng/ml, 5 ng/ml, 10 ng/ml, 20 ng/ml group, and can be seen fewer BFU-E in 5 ng/ml, 10 ng/ml, 20 ng/ml group, while the other group concentration did not see the erythroid clones.

3. Compared the clones of different concentration of TPA and G-CSF (50 ng/ml) stimulation in incomplete medium. Combination with G-CSF the better concentration of TPA is 1~10 ng/ml (both $P<0.05$). Combination with G-CSF the best concentration of TPA is 5 ng/ml and 1 ng/ml for CFU-GM and CFU-GEMM. The main clone types are myeloid colones, CFU-GM, also have CFU-GEMM and fewer BFU-E.

4. Compared the clones of four groups in complete medium, clones can be seen in four groups including of CFU-GM, CFU-GEMM, BFU-E, CFU-E. The clones of TPA with G-CSF group are highest compared with TPA group, G-CSF group and control group, difference have statistical significance (both $P<0.05$). While TPA group and G-CSF group the number of clones of TPA group and G-CSF group have no statistical significance ($P=0.577$).

5. Experiments show that TPA promote bone marrow stromal cells from healthy persons proliferation of concentration 5~10 ng/ml (cell number $2\times10^5$/ml). Decreasing or increasing the concentration of TPA, it shows that BMSCs are inhibited. Meanwhile, TPA promote bone marrow stromal cells from the AML patients proliferation of concentration 5~30 ng/ml (cell number 2×105/ml). 5 ng/ml of TPA is the best concentration of promoting proliferation, and G-CSF had no effect on the growth of BMSCs from healthy persons or AML patients.

Conclusion:

TPA promoted hematopoietic cell clone formation lonely, mainly of CFU-GM for bone marrow of AML patients in the period of bone marrow suppression in vitro, the best concentration is 10 ng/ml. TPA promoted the formation of CFU-GM, CFU-GEMM, and BFU-E at different stages.

TPA and G-CSF have synergistic effects in promoting bone marrow myeloid clones formation, in addition promote CFU-GEMM and BFU-E formation, the best concentration of TPA is 5 ng/ml. G-CSF promoted the formation of CFU-GM, but had no effect on CFU-GEMM and BFU-E.

TPA promoted the growth of the stroma cells of bone marrow (BMSCs) of the healthy human and the AML patient after chemotherapy, in the bone marrow suppression phase in vitro. The optimal concentrations were 5 ng/ml and 10 ng/ml.

As shown in FIG. 1, TPA stimulated the upstream stem cells to differentiate into downstream stem cells. GCSF only stimulated the downstream stem cells. TPA also stimulates downstream stem cells. Neutrophils are one type of granulocytes.

Example 2

Project TPA (PD616) for AML

MOA: Protein kinase C (PKC) activator
Indication:
1) current protocol: salvage therapy of AML after relapse
2) new strategy: AML supportive care after induction/consolidation chemotherapy on WBC and platelet recovery.
Rationale:
(1) Activation of PKC facilitates hematopoietic cells recovery
(2) PKC induces differentiation of leukemia cells
TPA in AML Strength
To enhance bone marrow recovery in 1 L AML after induction and consolidation chemotherapy
Well established mechanism of action by activation of PKC
Well known tolerable toxicity profile from prior clinical studies
Strong efficacy data in AML patients with potential shortening of neutropenia & thrombocytopenia duration from 20 to 12 days
Decrease hospital stay
Minimize chance of infection
Decrease the need of blood product support
Reduce AML patient care cost
TPA as a supportive care for white cell & platelets recovery after AML chemotherapy
Pitfalls of standard of care (SOC): G-CSF or GM-CSF does not work on early hematopoietic progenitor cells and with limited efficacy in shortening of the duration of neutropenia & thrombocytopenia after induction or consolidation therapy.
There is no effective approach to facilitate platelet recovery after chemotherapy in AML induction/consolidation.
TPA enhances growth of early progenitor cells and potentially helps shorten the duration of neutropenia and thrombocytopenia
Annual incidence 14,000 cases of AML, and 80% will receive aggressive chemo and develop prolonged neutropenia.
Target:
shortening of duration of neutropenia and hospital stay from 20 to 12 days,
Decrease blood products (PRBC and platelets) support, due to facilitation of platelet recovery
Decrease infection complication
No negative impact on efficacy, CR rate or duration of response
Indication
Shortening of neutropenia & thrombocytopenia in AML patients after induction or consolidation chemotherapy.
Shortening of neutropenia and thrombocytopenia.
Administration
TPA IV 3 times per week (M-W-F) until ANC over 1000 and platelets over 20,000 for at least 2 days at 0.125 mg/m$^2$ as a single course starting 24-48 hours after completion of chemotherapy whereas other supportive care remains as SOC.
Efficacy
Decrease the duration of neutropenia by 40%, from 20 days to 12 days. Decrease average hospitalization days by 40%. Decrease blood product support by 40%.
Safety
All toxicities not significantly worse than common toxicities associated with standard AML chemotherapy.
Competition
G-CSF and GM-CSF but not very effective
Phase 2 single arm study of 12 patients, TPA starts at 24-48 hours after completion of standard chemotherapy (6 for induction 3+7 and 6 for consolidation with 2+5 or high-dose Ara-C). TPA IV for M-W-F per week until ANC over 1000 and platelet over 20,000 persistently for 2+ days, whereas other supportive care same as SOC.
Double-blinded randomized phase 2, TPA+G-CSF vs. G-CSF in 1:1. 20 patients sample size with ~90% power and alpha 0.1, to detect a decrease of the duration of neutropenia & thrombocytopenia by 40% (from 20 days to 12 days)
Primary endpoints: Duration of neutropenia, blood product supports and hospitalization date all decreased by 40%.
Target goal of 40% reduction is achieved, and no obvious unfavorable effect to leukemia therapy.
Additional AML protocol includes starting TPA at 24-48 hours after completion of chemotherapy and watch duration of neutropenia & thrombocytopenia
Randomized phase 2 trial in two cohorts. One for induction chemotherapy, one for consolidation chemotherapy. Show duration of neutropenia decreased by 40%.

Example 3

This protocol is induction therapy, and does not include consolidation. This adjuvant therapy combines TPA and G-CSF (Granulocyte colony stimulating factor).

This is a single-arm, open label study. Ten (10) patients receive standard induction chemotherapy with idarubicin (12 mg/m2) or daunorubicin (60 mg/m2) on days 1, 2, 3 and Ara-C continuous (100-200 mg/m2/day) infusion on days 1-7. On Day 8 or 24 hours after completion of all scheduled Ara-C infusion, TPA is started at 0.125 mg/m² IV every two days, in addition to G-CSF (400 μg subcutaneously daily) support until absolute neutrophil count (ANC) above 1000/μL for two consecutive days."

A Phase 2a study of phorbol ester in shortening the duration of neutropenia and thrombocytopenia in acute myelocytic leukemia patients who receive induction chemotherapy.

Phorbol ester (12-O-Tetradecanoylphorbol-13-acetate, TPA) is an agonist of protein kinase C, and has been shown to increase early hematopoietic progenitor cells by in vitro studies. In prior Phase 1 dose escalation studies of TPA, TPA is observed to be capable of shortening the duration of post-chemotherapy neutropenia in acute myelocytic leukemia (AML) patients. In the recommended Phase 2 dose at 0.125 mg/m² daily up to 5 days a week×2 weeks, it is well tolerated with only minor adverse events such as shortness of breath, proteinuria, fever, chills and irritation of vein at infusion site. This study is designed to examine the efficacy of TPA as a supportive care agent to enhance bone marrow recovery in AML patients after induction chemotherapy.

Study objectives:
1. Evaluate the safety and tolerability of TPA in AML patients after induction chemotherapy
2. Evaluate preliminary efficacy in shortening of the duration of neutropenia and thrombocytopenia in AML patients after induction chemotherapy
3. Evaluate the preliminary Complete Remission (CR) rate after induction chemotherapy with maintenance TPA after induction therapy.

Eligibility

The inclusion criteria include:
1. Patients diagnosed with AML or advanced myelodysplastic syndrome (MDS, such as refractory anemia with excess blasts (RAEB), or RAEB with transformation), if their bone marrow blast count is over 20%.
2. AML should be classified by FAB classification, and all subtypes are allowed and recorded during enrollment, except patients with M3 or acute promyelocytic leukemia.
3. AML or advanced MSD patients who are considered suitable to receive 3+7 induction chemotherapy (anthracycline and cytarabine)
4. Age 18-70
5. ECOG 0-2
6. No evidence of major organ dysfunctions as defined by Creatinine ≤2 mg/dL, AST/ALT≤5×ULN, Bilirubin≤2 mg/dL, and no major cardiovascular problems such as recent acute myocardiac infarction or stroke within 6 months from enrollment.
7. Patients with adequate cardiac function without history of congestive heart failure as defined by no worse than American Heart Association class I (Patients with cardiac disease but resulting in no limitation of physical activity. Ordinary physical activity does not cause undue fatigue, palpitation, dyspnea or anginal pain).
8. Patients able to give consent for the study The exclusion criteria include:
1. Patients with other non-AML malignancies within the past 24 months, except those that are considered curable, such as treated basal cell carcinoma of skin, resected early stage malignancies such as ductal carcinoma in situ of breast and other cured cancers.
2. Patients with clinical active or chronic infection and not suitable for standard AML 3+7 induction therapy 3. Patients with recent major bleeding, surgery and other major medical problems within 6 months who are not suitable for standard AML 3+7 induction therapy.
4. Patients with chronic COPD who require chronic oxygen supplement to maintain pulse oxygen saturation above 92%.
5. Lactating and pregnant women
6. Patients with known positive HIV infection in the past Study Design This is a single-arm, open label study. Ten (10) patients receive standard induction chemotherapy with idarubicin (12 mg/m²) or daunorubicin (60 mg/m²) on days 1, 2, 3 and Ara-C continuous (100-200 mg/m²/day) infusion on days 1-7. On Day 9 or 24 hours after completion of all scheduled Ara-C infusion, TPA is started at 0.125 mg/m² IV every morning for 5 days on then 2 days off. Same 5 days on and 2 days off cycle of TPA administration is repeated once until patients' absolute neutrophil count (ANC) is above 1000/μL for two consecutive days. G-CSF at 400 μg subcutaneously or intravenously daily is started at the same day as the first day TPA starts but is administered in the afternoon, or approximately 8 hours after the morning dose of TPA. G-CSF is also stopped when patients' absolute neutrophil count (ANC) is above 1000/μL for two consecutive days. This sequential approach of administration of TPA followed by G-CSF is designed based on TPA stimulation of the proliferation of early progenitors such as CFU-GM and CFU-GEMM; whereas G-CSF stimulates the proliferation of later progenitor mainly CFU-GM or CFU-G. Without the expansion of early progenitor population, G-CSF would not have the target cell population and work effectively to enhance the recovery of normal white blood cells.

All other supportive care such as IV broad-spectrum antibiotics, anti-viral (such as anti-herpetic agents), and anti-fungal (such as anti-Candidiasis agents) support follow the standard practice guideline for AML induction therapy. Blood product support also follows the standard practice guideline with transfusion of packed red cells (PRBC) when hematocrit is below 30 and platelet count below 10,000 if no clinical evidence of bleeding (or 50,000 if clinical evidence of bleeding). All patients are hospitalized for the whole induction period until ANC and platelet recovery to adequate level without evidence of active infection. Standard care for neutropenia is adopted.

Study Duration

After patients recover from induction therapy, patients may be discharged from the hospital and return later for subsequent additional chemotherapy such as high dose Ara-C or considered for bone marrow transplantation per treating physician discretion based on their risk factors. Patients will be off study after they return for follow-up bone marrow evaluation for the efficacy of the induction therapy. All further consolidation therapy will not be considered part of the study.

Safety Evaluation

Safety analysis is evaluated based on Common Terminology Criteria for Adverse Events (CTCAE) vs. 4.0. The commonly observed adverse events includes shortness of breath, fever, chills and proteinuria. The treatment-related fever and chills are consistent with a cytokine increase after IV infusion of the study medication, but it is generally transient and subsides after 24 hours. Acetaminophen is used for symptomatic relief of the fever if necessary.

Efficacy Analysis

Evaluation of neutropenia and thrombocytopenia after induction chemotherapy is done by daily hematological tests, including complete blood count and differential count.

Day 14 bone marrow is routinely done according to the standard clinical practice guideline to assess any residual blasts 7 days after completion of induction therapy. Flow cytometry of the aspirated bone marrow is tested to differentiate the recovering normal progenitor cells versus residual blasts. The duration of neutropenia and thrombocytopenia is assessed separately and the ANC and platelet counts should be plotted in a diagram for each patient.

Statistics Analysis

The study explores the duration of neutropenia and thrombocytopenia after standard 3+7 induction chemotherapy in AML patients. Usually, 80% of AML patients will have a duration of neutropenia/thrombocytopenia of 20±3 days (i.e. ANC or platelet recovery at approximately at Days 24-30 assuming chemotherapy starts at Day 1) and then are discharged from the hospital if there is no evidence of infection. In the study, TPA shortens the duration of neutropenia and thrombocytopenia significantly. Duration of neutropenia or thrombocytopenia for patients treated with TPA is reduced to 12 days (ANC or platelet recovery at Day 14-24 days) with a standard deviation of 5 days, the sample size of 10 patients will have 90% power to detect a difference and reject the null hypothesis.

Example 4

Male patient, age 25, diagnosed with AML (M2). Patient's bone marrow myeloblast plus promyelocyte count was about 60%. After he received one standard course of DA regimen (7 Ara C+3 Daunorubicin), his peripheral WBC count dropped to $0.8 \times 10^9$/L. He was then administered 150 µg G-CSF each day. After chemotherapy, it took 12 days (duration of neutropenia and thrombocytopenia) to bring both his platelet count and WBC count, including the neutrophil count, back to normal. His bone marrow myeloblast plus promyelocyte count was about 40%, still way above the normal value (0~5%). Then, he received his second standard course of DA regimen. After the second course of DA regimen, his peripheral WBC count and platelet count dropped to $0.6 \times 10^9$/L and $80 \times 10^9$/L respectively. He was then administered TPA plus G-CSF (150 µg TPA followed with 150 µg G-CSF) each day of day 1 and day 2. On day 4 and day 5, he was administered with only 150 µg TPA each day. The WBC counts and neutrophil percentage* in parenthesis were $1.8 \times 10^9$/L (39%) on day 3, $6.5 \times 10^9$/L (72%) on day 7, and $5.7 \times 10^9$/L (77%) on day 14. The estimated duration of neutropenia after chemotherapy was shortened to about 5 days. The platelet counts were $330 \times 10^9$/L on day 3, $715 \times 10^9$/L on day 7, and $568 \times 10^9$/L on day 14. The estimated duration of thrombocytopenia after chemotherapy was shortened to less than 3 days. After one more course of DA regimen followed with TPA plus G-CSF treatment, his bone marrow myeloblast plus promyelocyte count was 2%, falling to the normal value.

*Neutrophils usually make up 60 to 70% of circulating WBC.

Example 5

Male patient, age 33, was diagnosed with myelodysplastic syndromes (MDS5q−). He had been treated with therapy which included EPO, G-CSF, thalidomide, and testosterone for 7 months without any improvement. His hematopoietic function was very low, especially erythropoiesis. His hemoglobin level was 40 g/L without blood transfusion. Besides receiving medication, he also had blood transfusion each month. After blood transfusion, his hemoglobin level reached 70-80 g/L. One to two weeks later, it dropped to 60 g/L. By the end of the month, it dropped to 40 g/L again. He had to receive blood transfusion again. He had suffered a loss of working ability and could not live a normal life. He was administered TPA+G-CSF+EPO treatment (TPA: 150-180 µg iv infusion+G-CSF: 150 µg im+EPO: 5000 unit im) 5 times. Each time, EPO and G-CSF were given 5 hours after TPA was given. After the 5 treatments of TPA+G-CSF with EPO, he maintained a hemoglobin level of 70 g/L without blood transfusion. He has ceased blood transfusions since then. His hemoglobin level continued to increase gradually the following two months and reached 120 g/L in three months after TPA+G-CSF+EPO treatment, close to the normal hemoglobin level (130-175 g/L). His WBC, RBC and platelet counts also gradually increased to nearly normal levels. He has recovered his daily work and normal life.

Example 6

Drug Induced Cytopenia Treated by TPA

Ninety (90) adult mice were randomly assigned to 9 groups (10 mice per group). No drug was administered in Control group. Model group was given DNR (6 mg/kg)+Ara-C (150 mg/kg) on Day 0. The rest of the 7 groups were given DNR (6 mg/kg)+Ara-C (150 mg/kg) on Day 0, and each group on Day 7, Day 8, and Day 9 was administered with one of the following drugs: G-CSF (10 µg/kg), EPO (500 IU/kg), TPA (12.5 µg/kg), TPA (25 µg/kg), TPA (50 µg/kg), TPA (12.5 µg/kg)+GCSF (10 µg/kg), or TPA (12.5 µg/kg)+EPO (500 IU/kg).

Experiment Model (3 Days after DNR+Ara-C)

TABLE 1

The comparison of blood cell counts between each group (n = 10)

| Group | Dose (mg · kg$^{-1}$) | WBC (×10$^9$/L) | RBC (×10$^{12}$/L) | PLT (×10$^9$/L) |
|---|---|---|---|---|
| Control | — | 6.47 ± 0.39 | 10.05 ± 0.43 | 1478 ± 125 |
| Model | DNR6 + Ara-c150 | 1.03 ± 0.26** | 9.91 ± 0.63 | 342 ± 59** |

Note:
Date represent means SD.
"*" P < 0.05,
"**" P < 0.01 vs control group

TABLE 2

The comparison of blood cell counts between each group (n = 10) (6 days after DNR + Ara-C)

| Group | Dose (mg · kg$^{-1}$) | WBC (×10$^9$/L) | RBC (×10$^{12}$/L) | PLT (×10$^9$/L) |
|---|---|---|---|---|
| Control | — | 6.72 ± 0.8 | 9.7 ± 0.48 | 1432 ± 79 |
| Model | DNR6 + Ara-c150 | 2.76 ± 0.61** | 6.04 ± 0.74** | 170 ± 51** |

Note:
Date represent means SD.
"*" P < 0.05,
"**" P < 0.01 vs control group

TABLE 3

The comparison of blood cell counts between each group (n = 10)
(8 days after DNR + Ara-c, 1 day after 1st TPA or other)

| Group | Dose (μg·kg$^{-1}$) | WBC (×10$^9$/L) | RBC (×10$^{12}$/L) | PLT (×10$^9$/L) |
|---|---|---|---|---|
| Control | — | 6.70 ± 0.17 | 10.05 ± 0.24 | 1439 ± 14.18 |
| Model | — | 3.30 ± 0.30①① | 5.02 ± 0.14①① | 98 ± 14.8①① |
| G-CSF | 10 | 5.3 ± 0.62②①② | 4.94 ± 0.42①① | 373 ± 76.27②②② |
| EPO | 500 | 3.7 ± 0.69①① | 7.32 ± 0.1G①①②② | 385 ± 19.28②②② |
| TPA | 12.5 | 6.4 ± 0.62②② | 6.08 ± 0.49①②②③④ | 395 ± 30.41②②② |
| TPA | 25 | 6.4 ± 0.35②② | 7.09 ± 0.23②②②②②③ | 391 ± 20.42②②② |
| TPA | 50 | 6.5 ± 0.75②② | 7.10 ± 0.24②②②②③ | 413 ± 9.64②②② |
| TPA + GCSF | 12.5 + 10 | 8.5 ± 0.46②②②②③⑤ | 6.22 ± 0.61①①②②③ | 405 ± 47.62②②② |
| TPA + EPO | 12.5 + 500 | 6.8 ± 0.79②②④⑤ | 8.61 ± 0.27②②②②⑤ | 417 ± 45.3①②② |

Note:
Date represent means SD.

"①" P < 0.05,

"①①" P < 0.01 vs control group;

"②" P < 0.05,

"②②" P < 0.01 vs model group,

"③" P < 0.05,

"③③" P < 0.01 vs G-CSF group

"④" P < 0.05,

"④④" P < 0.01 vs EPO group

"⑤" P < 0.05,

"⑤⑤" P < 0.01 vs TPA 12.5 μg·kg$^{-1}$ group

TABLE 4

The comparison of blood cell counts between each group (n = 10)
(9 days after DNR + Ara-c, 1 day after 2nd TPA or other)

| Group | Dose (μg·kg$^{-1}$) | WBC (×10$^9$/L) | RBC (×10$^{12}$/L) | PLT (×10$^9$/L) |
|---|---|---|---|---|
| Control | — | 6.72 ± 0.81 | 9.74 ± 0.48 | 1432 ± 79.28 |
| Model | — | 5.46 ± 0.49①① | 5.45 ± 0.68①① | 512 ± 42.99①① |
| G-CSF | 10 | 6.95 ± 0.44② | 5.40 ± 0.46①① | 949 ± 65.88②②② |
| EPO | 500 | 5.52 ± 0.34①① | 6.75 ± 0.69①①② | 935 ± 43.57②②② |
| TPA | 12.5 | 6.84 ± 0.44② | 7.47 ± 0.55①②②④ | 965 ± 76.23②②② |
| TPA | 25 | 6.72 ± 0.50② | 7.34 ± 0.87①①②② | 951 ± 70.29②②② |
| TPA | 50 | 6.86 ± 0.39② | 7.30 ± 0.49①①②② | 999 ± 45.67②②② |
| TPA + GCSF | 12.5 + 10 | 10.74 ± 0.58①①②②③⑤ | 7.18 ± 0.38①②②④ | 969 ± 52.86②②② |
| TPA + EPO | 12.5 + 500 | 6.78 ± 0.34④ | 8.87 ± 0.29②②②④ | 928 ± 32.72②②② |

Note:
Date represent means SD.

"①" P < 0.05,

"①①" P < 0.01 vs control group;

"②" P < 0.05,

"②②" P < 0.01 vs model group,

"③" P < 0.05,

"③③" P < 0.01 vs G-CSF group

"④" P < 0.05,

"④④" P < 0.01 vs EPO group

"⑤" P < 0.05,

"⑤⑤" P < 0.01 vs TPA 12.5 μg·kg$^{-1}$ group

TABLE 5

The comparison of blood cell counts between each group (n = 10)
(10 days after DNR + Ara-c, 1 day after 3rd TPA or other)

| Group | Dose (μg·kg$^{-1}$) | WBC (×10$^9$/L) | RBC (×10$^{12}$/L) | PLT (×10$^9$/L) |
|---|---|---|---|---|
| Control | — | 6.60 ± 0.54 | 9.96 ± 0.82 | 1425 ± 52.34 |
| Model | — | 6.55 ± 0.61 | 5.17 ± 0.56①① | 730 ± 71.09①① |
| G-CSF | 10 | 9.14 ± 0.67②②② | 5.30 ± 0.34①① | 1456 ± 91.76②② |
| EPO | 500 | 6.45 ± 0.41③③ | 8.51 ± 0.86①①②②③ | 1469 ± 75.67②② |
| TPA | 12.5 | 9.51 ± 0.85①②②④ | 7.59 ± 0.67①①②②③ | 1447 ± 78.09②② |
| TPA | 25 | 9.69 ± 0.85②②②④ | 8.26 ± 0.63②②②②②⑤ | 1465 ± 72.81②② |

TABLE 5-continued

The comparison of blood cell counts between each group (n = 10)
(10 days after DNR + Ara-c, 1 day after 3rd TPA or other)

| Group | Dose (μg · kg$^{-1}$) | WBC (×10$^9$/L) | RBC (×10$^{12}$/L) | PLT (×10$^9$/L) |
|---|---|---|---|---|
| TPA | 50 | 9.90 ± 0.64[①①②④] | 8.18 ± 0.55[①②③④⑤] | 1463 ± 80.33[②②] |
| TPA + GCSF | 12.5 + 10 | 9.90 ± 0.63[①①②] | 7.47 ± 0.64[①①②②③③] | 1419 ± 89.66[②②] |
| TPA + EPO | 12.5 + 500 | 9.44 ± 0.3G[①②③④] | 10.18 ± 0.19[②②③④⑤] | 1430 ± 71.47[②②] |

Note:
Date represent means SD.
"①" P < 0.05,
"①①" P < 0.01 vs control group;
"②" P < 0.05,
"②②" P < 0.01 vs model group,
"③" P < 0.05,
"③③" P < 0.01 vs G-CSF group
"④" P < 0.05,
"④④" P < 0.01 vs EPO group
"⑤" P < 0.05,
"⑤⑤" P < 0.01 vs TPA12.5 μg · kg$^{-1}$ group

CONCLUSION

1) TPA promoted the production of WBC, RBC, and platelet. It could be useful to treat different forms of cytopenia, such as anemia, leukopenia, neutropenia, thrombocytopenia, granulocypenia, pancytopenia, and hypocytopenia (see https at en.wikipedia.org/wiki/Cytopenia).
2) TPA combined with G-CSF has a synergistic effect in promoting the production of WBC.
3) TPA combined with EPO has a synergistic effect in promoting the production of RBC.
4) TPA may promote the hematopoietic pathway on different stages, from upstream myeloid stem cells to differentiate towards downstream stem cells and then from downstream stem cells to further differentiate to different blood cells.

I claim:

1. A method of treating neutropenia and/or anemia comprising administering to a mammalian subject in need thereof, a combination of a phorbol ester of Formula I, pharmaceutically-acceptable salt, isomer, enantiomer, solvate, hydrate, or polymorph thereof,

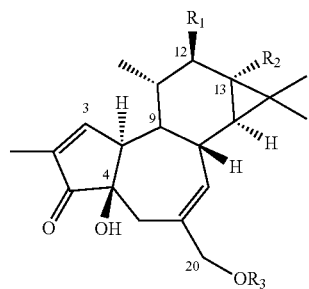

Formula I wherein $R_1$ and $R_2$ are selected from the group consisting of hydrogen, hydroxyl,

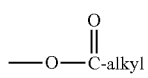

wherein the alkyl group contains 1 to 15 carbon atoms,

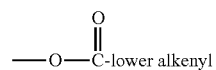

wherein the lower alkenyl group contains 1 to 7 carbon atoms,

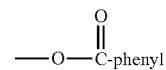

and

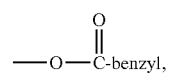

$R_3$ is hydrogen or $$—O—\overset{O}{\underset{\|}{C}}\text{-lower alkyl;}$$

and a granulocyte-colony stimulating factor (G-CSF); wherein said phorbol ester of Formula I is administered in an effective amount from about 10 and 1500 μg of said phorbol ester of Formula I per day, and said G-CSF is administered in an effective amount from 150 μg to 400 μg; wherein the G-CSF is administered to said mammalian subject in a coordinate administration protocol, simultaneously with, or after administration of said phorbol ester of Formula I; and wherein the combination of phorbol ester of Formula I and G-CSF is administered at least two times.

2. A method of treating neutropenia and/or thrombocytopenia comprising administering to a mammalian subject in need thereof, a combination of a phorbol ester of Formula I, pharmaceutically-acceptable salt, isomer, enantiomer, solvate, hydrate, or polymorph thereof, Formula I

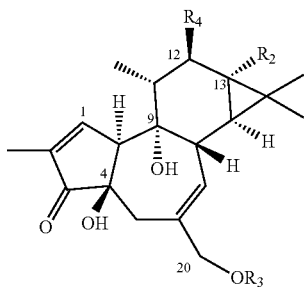

wherein $R_1$ and $R_2$ are selected from the group consisting of hydrogen,

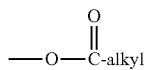

wherein the alkyl group contains 1 to 15 carbon atoms,

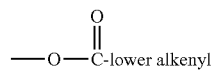

wherein the lower alkenyl group contains 1 to 7 carbon atoms, and

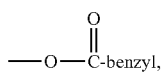

$R_3$ is hydrogen or

and a granulocyte-colony stimulating factor (G-CSF); wherein said phorbol ester of Formula I is administered in an effective amount from about 10 and 1500 μg of said phorbol ester of Formula I per day, and said G-CSF is administered in an effective amount from 150 μg to 400 μg; wherein the G-CSF is administered to said mammalian subject in a coordinate administration protocol, simultaneously with, or after administration of said phorbol ester of Formula I; and wherein the combination of phorbol ester of Formula I and G-CSF is administered at least two times.

3. The method according to claim 1 or 2, wherein $R_1$ or $R_2$ is

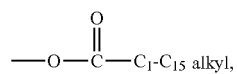

the remaining $R_1$ or $R_2$ is

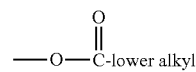

and $R_3$ is hydrogen.

4. The method according to claim 1 or 2, wherein the phorbol ester is phorbol 13-butyrate, phorbol 12-decanoate, phorbol 13-decanoate, phorbol 12,13-diacetate, phorbol 13,20-diacetate, phorbol 12,13-dibenzoate, phorbol 12,13-dibutyrate, phorbol 12,13-didecanoate, phorbol 12,13-dihexanoate, phorbol 12,13-dipropionate, phorbol 12-myristate, phorbol 13-myristate, phorbol 12,13,20-triacetate, 12-deoxyphorbol 13-angelate, 12-deoxyphorbol 13-angelate 20-acetate, 12-deoxyphorbol 13-isobutyrate, 12-deoxyphorbol 13-isobutyrate-20-acetate, 12-deoxyphorbol 13-phenylacetate, 12-deoxyphorbol 13-phenylacetate 20-acetate, 12-deoxyphorbol 13-tetradecanoate, phorbol 12-tigliate 13-decanoate, 12-deoxyphorbol 13-acetate, phorbol 12-acetate, or phorbol 13-acetate.

5. The method according to claim 1 or 2, wherein the phorbol ester is 12-O-tetradecanoylphorbol-13-acetate (TPA).

6. The method according to claim 1 or 2, further comprising administering at least one secondary or adjunctive therapeutic agent.

7. The method according to claim 1 or 2, wherein said phorbol ester of Formula I is administered every day or every other day.

8. The method according to claim 1 or 2, wherein said phorbol ester of Formula I is administered in an effective amount comprising between about 150 to 500 μg of said phorbol ester compound of Formula I every day or every other day.

9. The method according to claim 1 or 2, wherein the combination increases absolute neutrophil count (ANC) of the mammalian subject to above 1500/mm$^3$.

10. The method according to claim 1 or 2, wherein the combination increases platelet levels of the mammalian subject to above 100,000/μl.

11. The method according to claim 1 or 2, wherein the mammalian subject is a human with acute myeloid leukemia (AML).

* * * * *